(12) United States Patent
Lee et al.

(10) Patent No.: US 10,537,246 B2
(45) Date of Patent: Jan. 21, 2020

(54) MULTIPLE IMPLANT COMMUNICATIONS WITH ADJUSTABLE LOAD MODULATION BASED ON RECEIVED SIGNAL AMPLITUDES

(71) Applicant: The Alfred E. Mann Foundation for Scientific Research, Valencia, CA (US)

(72) Inventors: Edward K. F. Lee, Fullerton, CA (US); Harshit R. Suri, Pasadena, CA (US)

(73) Assignee: THE ALFRED E. MANN FOUNDATION FOR SCIENTIFIC RESEARCH, Valencia, CA (US)

( * ) Notice: Subject to any disclaimer, the term of this patent is extended or adjusted under 35 U.S.C. 154(b) by 0 days.

(21) Appl. No.: 15/890,509

(22) Filed: Feb. 7, 2018

(65) Prior Publication Data
US 2018/0220891 A1 Aug. 9, 2018

Related U.S. Application Data

(60) Provisional application No. 62/456,576, filed on Feb. 8, 2017.

(51) Int. Cl.
*A61B 5/00* (2006.01)
*A61N 1/372* (2006.01)
*H04B 14/00* (2006.01)

(52) U.S. Cl.
CPC .......... *A61B 5/0022* (2013.01); *A61B 5/0031* (2013.01); *A61N 1/37288* (2013.01);
(Continued)

(58) Field of Classification Search
CPC ... A61B 5/0022; A61B 5/0015; A61B 5/0031; A61B 5/7228; A61B 2562/12;
(Continued)

(56) References Cited

U.S. PATENT DOCUMENTS 4,564,823 A * 1/1986 Stahler ................. H04B 14/002
329/341
7,515,654 B2 * 4/2009 Umetani ................ H04L 25/062
369/59.17
(Continued)

OTHER PUBLICATIONS

PCT International Search Report for PCT/US2018/017201, Applicant: The Alfred E. Mann Foundation for Scientific Research, Form PCT/ISA/210 and 220, dated May 3, 2018 (6pages).
(Continued)

*Primary Examiner* — Franklin D Balseca
(74) *Attorney, Agent, or Firm* — Michael J. Bolan; Vista IP Law Group, LLP

(57) ABSTRACT

A medical system and method of communicating between a telemetry controller and medical devices is provided. Coupling coefficients between a primary coil of the telemetry controller and secondary coils of the medical devices differ from each other. A primary carrier signal is applied to the primary coil, thereby respectively inducing secondary carrier signals on the secondary coils. An amplitude of the secondary carrier signal is measured on each of the secondary coils. The envelope of each secondary carrier signal is modulated in accordance with data, thereby inducing modulation of the envelope of the primary carrier signal for the implanted medical devices. The secondary carrier signal envelopes are modulated based on the measured amplitudes of the respective secondary carrier signals.

29 Claims, 14 Drawing Sheets

(52) U.S. Cl.
CPC .......... *A61B 5/0015* (2013.01); *A61N 1/3727* (2013.01); *A61N 1/37282* (2013.01); *H04B 14/004* (2013.01)

(58) Field of Classification Search
CPC .............. A61N 1/37288; A61N 1/3727; A61N 1/37282; H04B 14/004; H04L 27/02
See application file for complete search history.

(56) References Cited

U.S. PATENT DOCUMENTS

| | | | |
|---|---|---|---|
| 8,577,327 B2* | 11/2013 | Makdissi | A61B 5/0028 455/343.1 |
| 2010/0189196 A1 | 7/2010 | Wang et al. | |
| 2013/0215979 A1 | 8/2013 | Yakovley et al. | |
| 2018/0013596 A1* | 1/2018 | Nakano | G06K 19/07 |
| 2018/0028824 A1* | 2/2018 | Pivonka | A61N 1/37288 |

OTHER PUBLICATIONS

PCT Written Opinion of the International Search Authority for PCT/US2018/017201, Applicant: The Alfred E. Mann Foundation for Scientific Research, Form PCT/ISA/237, dated May 3, 2018 (8pages).

\* cited by examiner

MULTIPLE IMPLANT COMMUNICATIONS WITH ADJUSTABLE LOAD MODULATION BASED ON RECEIVED SIGNAL AMPLITUDES

CLAIM OF PRIORITY

Pursuant to 35 U.S.C. § 119(e), this application claims the benefit of U.S. Provisional Patent Application 62/456,576, filed Feb. 8, 2017, which is expressly incorporated herein by reference.

FIELD OF THE INVENTION

The present invention generally relates to wireless power/data transfer techniques in medical systems, and specifically relates to such techniques for use in wirelessly providing power to and receiving uplink data from multiple implantable devices.

BACKGROUND OF THE INVENTION

In the field of wireless power and data transfer, inductive coupling has been used to provide power to and communicate with a device without making electrical contact. This technique has been used, for example, with medical systems comprising multiple medical devices that can be implanted inside of the body of a patient. Medical systems utilizing this technique have an external control unit, such as a telemetry controller (TC), and one or more medical devices implanted within the body of a patient. Power transfer and data communication between the external control unit and implanted medical device(s) are provided via an inductive link.

For example, as illustrated in FIG. 1, a conventional power/data transfer system 10 typically includes an external TC 12 capable of performing a medical function (which could be diagnostic and/or therapeutic) and a plurality of implantable medical devices ("implants") 14, (only two implants 14(y), 14(z) are shown for purposes of brevity in illustration), each of which is capable of sensing physiological signals in the body of a patient and transmitting representative data to the TC 12 in furtherance of performing the medical function.

A primary coil Lp located inside the TC 12 inductively couples and powers secondary coils Ls(y), Ls(z) respectively inside the implanted medical devices 14(y), 14(z). Power is delivered to the implanted medical devices 14 by applying an alternating current (AC) current on the primary coil Lp at a selected transmission frequency Ft. Capacitors Cs(y), Cs(z) are respectively coupled in parallel to the secondary coils Ls(y), Ls(z) to form LC tank circuits that are tuned to resonate at the transmission frequency Ft. In addition to providing power to the medical devices, the coils Lp's and Ls's are also utilized for communication between the TC 12 and the implanted medical devices 14. For downlink data from the TC 12 to the implanted medical devices 14, different modulation techniques can be applied to the AC current on the primary coil Lp.

For uplink data from the implanted medical devices 14 to the TC 12, a load modulation technique can be used. In this technique, each implanted medical device 14 transmits uplink data to the TC 12 in a given time slot in a time-division multiplexed manner by modulating a load resistance Rs to a modified load resistance Rs+ΔRs according to the uplink data, where $\Delta R_L$ is the amount of change on the load resistance. Due to the inductive coupling between the primary coil Lp and the corresponding secondary coil Ls, a voltage amplitude change on the primary coil Lp according to the uplink data is obtained. Based on the amplitude change, the TC 12 can demodulate the data sent from a particular implanted medical device 14 at the corresponding time slot utilizing any one or more of a variety of demodulation techniques, including amplitude shift keying (ASK), phase shift keying (PSK), frequency shift keying (FSK), etc.

The amplitudes of the signals received by the TC 12 from the implanted medical devices 14 may different from each other. For example, depending on the distances, as well as the characteristic of the material, between the primary coil Lp and the secondary coils Ls(y), Ls(z), the coupling coefficients Kc(y), Kc(z) between the primary coil Lp and the respective secondary coils Ls(y), Ls(z) can be different for the different implanted medical devices 14(y), 14(z). The difference in the respective coupling coefficients Kc(y), Kc(z) between the primary coil Lp and the secondary coils Ls(y), Ls(z) will affect the voltage amplitudes on different secondary coils Ls(y), Ls(z). Furthermore, if each medical device 14 utilizes the same amount of load resistance change ΔRs for load modulating the uplink data, the voltage amplitude induced on the primary coil Lp for each implanted medical device 14 will also be different. These voltage amplitude differences on the primary coil Lp due to different coupling coefficients Kc(y), Kc(z) will complicate the circuitry inside the TC 12 that demodulates the uplink data from the induced voltage on the primary coil Lp. Thus, the received signal amplitudes corresponding to the respective implanted medical devices 14(y), 14(z) may be primarily affected by the coupling coefficients Kc(y), Kc(z). The received signal amplitudes corresponding to the respective implanted medical devices 14(y), 14(z) may also be secondarily affected by the different tuning tolerances between the primary coil Lp and the respective secondary coils Ls(y), Ls(z).

For example, referring to FIG. 2, the changes in the amplitude of AC voltage induced on the primary coil Lp due to load modulations at the secondary coils Ls are represented as changes in an envelope signal Senv. A simple demodulator design utilizes an envelope detector to extract the envelope signal Senv from the amplitude changes induced on the primary coil Lp, and a comparator to compare the envelope signal Senv with an appropriate threshold level Sth to determine the uplink data. In the embodiment illustrated in FIG. 2, an ASK modulation technique is employed to encode the envelope signal Senv with data that can then be demodulated to acquire the data therefrom.

For example, as shown in FIG. 3a, an ASK modulated envelope signal Senv1, which contains one of two bits of information ("1" or "0") during each symbol period (indicated between the dashed lines), can be converted into a digital signal by comparing the envelope signal Senv1 to a threshold level Sth. The data value can be read as switching between "0" and "1" if and when the envelope signal Senv1 crosses the threshold level Sth in the respective symbol period, i.e., from "0" to "1" when the envelope signal Senv1 rises above the threshold level Sth, and from "1" to "0" when the envelope signal Senv1 falls below the threshold level Sth.

In an alternative embodiment shown in FIG. 3b, a four-phase (0°, 90°, 180°, and) 270° PSK modulated envelope signal Senv2, which contains two bits of information ("00," "01," "10," and "11") during each symbol period (indicated between the dashed lines), can be converted into a digital signal by comparing the envelope signal Senv2 to a threshold level Sth. The data value can be read as being "00," "01,"

"10," and "11," depending on when and in what direction the envelope signal Senv2 crosses the threshold level Sth in the respective symbol period.

In still another alternative embodiment shown in FIG. 3c, an FSK modulated envelope signal Senv3, which contains one of two bits of information ("1" or "0") during each symbol period (indicated between the dashed lines), can be converted into a digital signal by comparing the envelope signal Senv3 to a threshold level Sth. The data value can be read as "0" and "1," depending on how many times the envelope signal Senv3 crosses the threshold level Sth in the respective symbol period, i.e., a "0" if the envelope signal Senv crosses the threshold level Sth three or less times (resulting from the relatively low-frequency portion of the envelope signal Senv), a "1" if the envelope signal Senv cross the threshold level Sth more than three times (resulting from the relatively high-frequency portion of the envelope signal Senv3)

Regardless of the type of demodulation technique, when the coupling coefficients Kc between the primary coil Lp and the secondary coils Ls(y), Ls(z) of the implanted medical devices $14(y)$, $14(z)$ differ, the peak-to-peak amplitudes of the envelope signals Senv on the primary coil Lp for the implanted medical devices $14(y)$, $14(z)$ will be different. In this case, the peak-to-peak amplitude of the envelope signal Senv for the implanted medical device $14(y)$ with a relatively high coupling coefficient Kc(y) will be greater than the peak-to-peak amplitude of the envelope signal Senv for the implanted medical device $14(z)$ with a relatively low coupling coefficient Kc(z). Thus, different threshold level values St(y), St(z) are respectively required to correctly demodulate the uplink data for the implanted medical devices $14(y)$, $14(z)$.

Because a single threshold level value St cannot be used to demodulate the uplink data from the different implanted medical devices 14, a more complicated demodulator design utilizing equalization techniques for the envelope signals Senv is required. If the coupling coefficients Kc drift in time, an even more complicated demodulator design using adaptive equalization will become necessary. Alternatively, AC coupling can be used between the envelope detector and the comparator, such that the average value of the envelope signal Senv for the uplink data sent by the different implanted medical devices 14 will move to ground, and thus, the threshold level St can be set to ground. The uplink data can therefore be correctly demodulated from the envelope signal Senv. However, because it will take some time to have the average value of the envelope signal Senv to move to ground at the output of the AC coupling whenever a different implanted medical device sends out uplink data, the data within the time required for settling the average value of the envelope signal Senv to ground cannot be reliably detected without significantly reducing the uplink data transmission rate.

There, thus, remains a need for providing a simpler means that allows demodulation of uplink data sent from multiple implantable medical devices without having to reduce the uplink data transmission rate.

SUMMARY OF THE INVENTION

In accordance with a first aspect of the present inventions, a medical system comprises a telemetry controller (e.g., an external telemetry controller) a primary coil, a coil driver configured for applying a primary carrier signal having an envelope capable of being modulated to the primary coil, and a demodulator configured for amplitude demodulating the modulated primary carrier signal envelope to acquire data. In one embodiment, the demodulator is configured for amplitude demodulating the modulated primary carrier signal envelope by detecting the modulated primary carrier signal envelope, and comparing the detected envelope of the primary carrier signal to a threshold level. In this case, the amplitude of the threshold level may be between a minimum and a maximum of the modulated primary carrier signal envelope, e.g., centered between the minimum and the maximum of the modulated primary carrier signal envelope.

The medical system further comprises a plurality of implantable medical devices, each of which comprises a secondary coil on which a secondary carrier signal having an envelope may be induced in response to the application of the primary carrier signal on the primary coil, an amplitude detector configured for measuring an amplitude of the secondary carrier signal, and a modulator configured for amplitude modulating the secondary carrier signal envelope in accordance with data, thereby inducing an amplitude modulation of the primary carrier signal envelope on the primary coil. In one embodiment, the data is physiological data of the patient, in which case, each of the implantable medical devices may further comprise at least one sensor configured for acquiring the physiological data from the patient. In other embodiments, the data may be operational status data of each of the implantable medical devices.

The modulators of the implantable medical devices are configured for modulating the secondary carrier signal envelopes (e.g., via load modulation) based on the measured amplitudes (e.g., peak amplitudes) of the respective secondary carrier signals, such that a variation of the amplitude modulation of the primary carrier signal envelope between the implanted medical devices is decreased to compensate for different coupling coefficients between the primary coil and the secondary coils. In one embodiment, the amplitude detector of each of the implantable medical devices is configured for measuring the amplitude of the secondary carrier signal on the respective secondary coil by measuring a voltage across the respective secondary coil, and the modulator of each of the implantable medical devices is configured for amplitude modulating the envelope of the secondary carrier signals by modifying a load current associated with the secondary coil as a function of the measured voltage.

In another embodiment, the primary carrier signal envelope is substantially uniformly amplitude modulated for the implanted medical devices. For example, a variation in modulation amplitude of the primary carrier signal envelope between the implanted medical devices may be less than 50%, and preferably, less than 20%. In still another embodiment, the modulators are configured for modulating the envelopes of the secondary carrier signals, such that modulation magnitudes of the modulated envelopes of the secondary carrier signals vary in an inversely varying relationship with the coupling coefficients between the respective secondary coils and the primary coil. In an optional embodiment, each of the implantable medical devices further comprises a rectifier configured for rectifying and regulating the secondary carrier signal for powering circuitry within the respective implantable medical device.

In accordance with a second aspect of the present inventions, a method of communicating between a telemetry controller (which may be external) and a plurality of medical devices implanted within a patient is provided. The telemetry controller has a primary coil and each of the medical devices has a secondary coil, and coupling coefficients between the primary coil and the secondary coils differ from each other.

The method comprises applying a primary carrier signal having an envelope to the primary coil, thereby respectively inducing a secondary carrier signal having an envelope on each of the secondary coils, generating data by each of the implanted medical devices, and measuring an amplitude of the secondary carrier signal on each of the secondary coils. In one method, the generated data may be physiological data acquired from the patient by each of the implantable medical devices. In other methods, the generated data may be operational status data of each of the implantable medical devices.

The method further comprises sequentially amplitude modulating each of the secondary carrier signal envelopes in accordance with the data generated by the respective implanted medical device, thereby inducing an amplitude modulation of the primary carrier signal envelope on the primary coil for the implanted medical devices. In one method, the primary carrier signal envelope is substantially uniformly amplitude modulated for the implanted medical devices. For example, a variation in modulation amplitude of the primary carrier signal envelope between the implanted medical devices may be less than 50%, and preferably, less than 20%.

The secondary carrier signal envelopes are modulated (e.g., via load modulation) based on the measured amplitudes (e.g., peak amplitudes) of the respective secondary carrier signals, such that a variation of the amplitude modulation of the primary carrier signal envelope between the implanted medical devices is decreased to compensate for the different coupling coefficients. In one method, each of the secondary carrier signal envelopes is modulated, such that modulation magnitudes of the modulated envelopes of the secondary carrier signals vary in an inversely varying relationship with the coupling coefficients between the respective secondary coils and the primary coil. In another method, measuring the amplitude of the secondary carrier signal on each of the secondary coils comprises measuring a voltage across the respective secondary coil, and amplitude modulating the envelope of each of the secondary carrier signals comprises modifying a load current associated with the secondary coil as a function of the measured voltage.

The method further comprises amplitude demodulating the modulated primary carrier signal envelope to acquire the data from the implanted medical devices. In one method, amplitude demodulating the modulated primary carrier signal envelope comprises detecting the modulated primary carrier signal envelope, and comparing the detected envelope of the primary carrier signal to a threshold level. In this case, the amplitude of the threshold level may be between a minimum and a maximum of the modulated primary carrier signal envelope, e.g., centered between the minimum and the maximum of the modulated primary carrier signal envelope. An optional method comprises generating power for each of the implanted medical devices from the respective secondary carrier signal.

In accordance with a third aspect of the present inventions, an implantable medical device for communicating with a telemetry controller having a primary coil on which a primary carrier signal is applied is provided. The implantable medical device comprises a secondary coil on which a secondary carrier signal having an envelope may be induced in response to the application of the primary carrier signal on the primary coil. The implantable medical device further comprises an amplitude detector configured for measuring an amplitude (e.g., peak amplitude) of the secondary carrier signal, processing circuitry configured for selecting a magnitude of a modulation of the secondary carrier signal in accordance with an inversely varying relationship with the measured amplitude of the secondary carrier signal, and a modulator configured for applying the selected modulation magnitude to the secondary carrier signal envelope (e.g., via load modulation) in accordance with data, thereby inducing an amplitude modulation of the primary carrier signal envelope on the primary coil. In one embodiment, the data is physiological data of the patient, in which case, the implantable medical devices may further comprise at least one sensor configured for acquiring the physiological data from the patient. In other embodiments, the data may be operational status data of the implantable medical devices.

In one embodiment, the amplitude detector is configured for measuring the amplitude of the secondary carrier signal by measuring a voltage across the secondary coil, and the modulator is configured for amplitude modulating the envelope of the secondary carrier signal by modifying a load current associated with the secondary coil. In an optional embodiment, the implantable medical device further comprises a rectifier configured for rectifying and regulating the secondary carrier signal for powering circuitry within the implantable medical device. The implantable medical device may comprise a biocompatible casing containing the secondary coil, amplitude detector, processing circuitry, and modulator.

In accordance with a fourth aspect of the present invention, a method of communicating between a telemetry controller (which may be external) and a medical device implanted within a patient is provided. The telemetry controller has a primary coil, and the medical device has a secondary coil. The method comprises generating data by the implanted medical device, and applying a primary carrier signal having an envelope to the primary coil, thereby respectively inducing a secondary carrier signal having an envelope on the secondary coil. In one method, the generated data may be physiological data acquired from the patient by the implantable medical device. In other methods, the generated data may be operational status data of the implantable medical device.

The method further comprises measuring an amplitude (e.g., a peak amplitude) of the secondary carrier signal on the secondary coils, selecting a magnitude of a modulation of the secondary carrier signal in accordance with an inversely varying relationship with the measured amplitude of the secondary carrier signal, and applying the selected modulation magnitude to the secondary carrier signal envelope (e.g., via load modulation) in accordance with the physiological data acquired by the implanted medical device, such that the primary carrier signal envelope is amplitude modulated. In one method, measuring the amplitude of the secondary carrier signal on the secondary coil may comprise measuring a voltage across the secondary coil, and wherein amplitude modulating the envelope of the secondary carrier signal comprises modifying a load current associated with the secondary coil.

The method further comprises amplitude demodulating the modulated primary carrier signal envelope to acquire the physiological data from the implanted medical device. In one method, amplitude demodulating the modulated primary carrier signal envelope may comprise detecting the modulated primary carrier signal envelope, and comparing the detected envelope of the primary carrier signal to a threshold level. In this case, the amplitude of the threshold level may be centered between a minimum and a maximum of the modulated primary carrier signal envelope.

In accordance with a fifth aspect of the present inventions, a method of manufacturing an implantable medical device is provided. The method comprises (a) selecting a uniform value for an amplitude modulation induced on a primary signal envelope, and (b) selecting a coupling coefficient value between a primary coil and secondary coil. The method further comprises (c) applying a fixed alternating current (AC) signal to the primary coil, thereby respectively inducing a secondary signal on the secondary coil for the selected coupling coefficient value, (d) determining an amplitude of the secondary signal (e.g., a peak amplitude) for the coupling coefficient value, and (e) determining an amplitude of a modulating signal for modulating an envelope of the secondary signal in a manner that induces an amplitude modulation on the primary coil that is substantially equal to the selected uniform amplitude modulation value, e.g., by adjusting the modulating signal until the amplitude modulation induced on the primary signal envelope is substantially equal to the selected uniform amplitude modulation value. In one method, determining the amplitude of the secondary carrier signal on the secondary coil comprises determining a voltage across the secondary coil, in which case, the modulating signal may define a change in a current in the secondary coil. Steps (c)-(e) may, e.g., be simulated or actually performed.

The method further comprises (f) correlating the determined amplitude of the secondary signal and the determined amplitude of the modulating signal to create a data point, and (g) repeating steps (b)-(f) for different coupling coefficient values to create a plurality of data points. The method further comprises (h) deriving a relationship between the respective amplitudes of the secondary signal and the modulating signal from the plurality of data points, and (i) manufacturing the implantable medical device having the secondary coil and processing circuitry configured for outputting a modulating signal in response to an input of a measured amplitude of a secondary carrier signal induced on the secondary coil in accordance with the derived relationship, such that an envelope of the secondary carrier signal is modulated.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
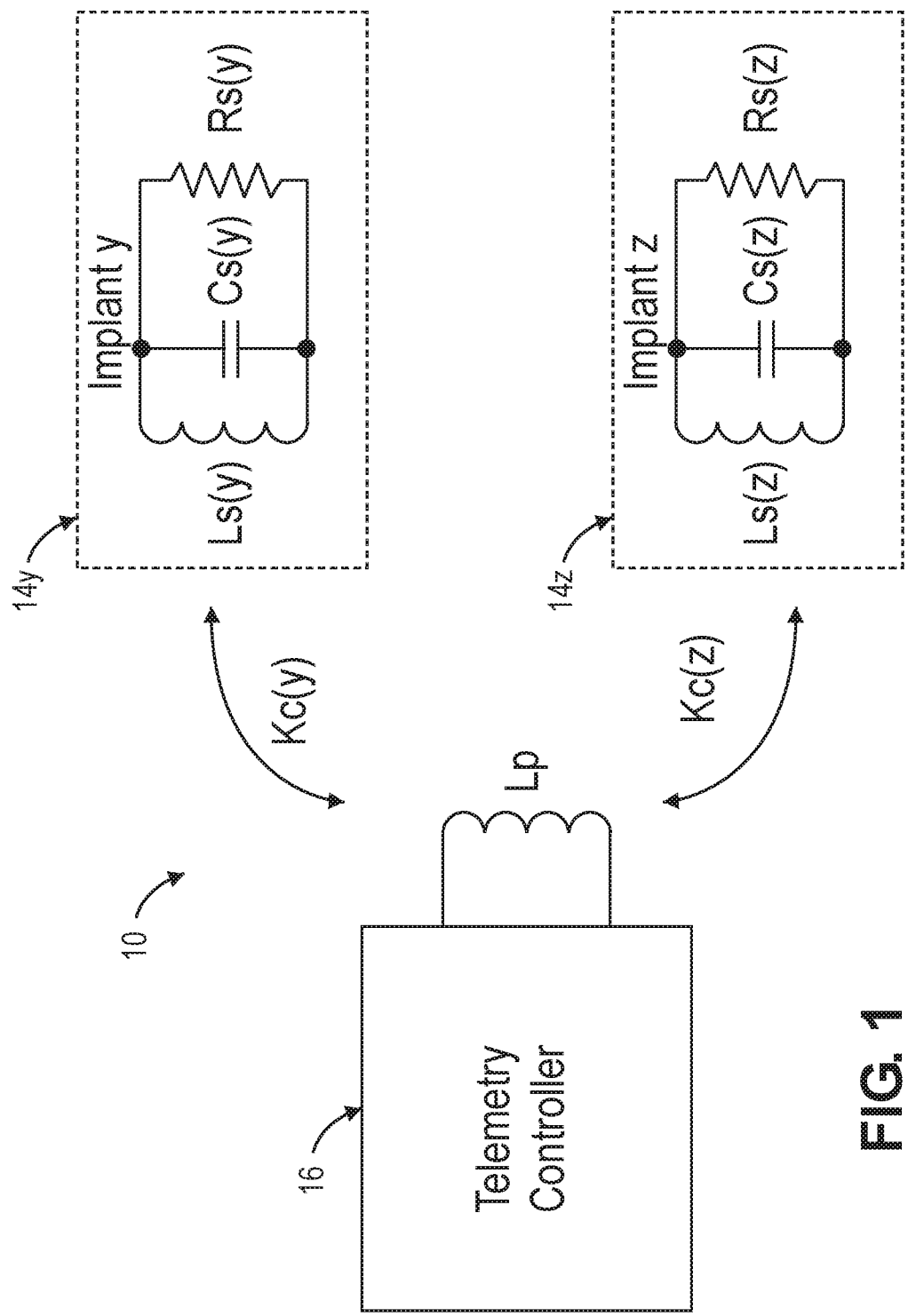
FIG. 1 is a block diagram of a prior art power/data transfer system for powering and communicating with implantable medical devices via a telemetry controller.
Figure 2:
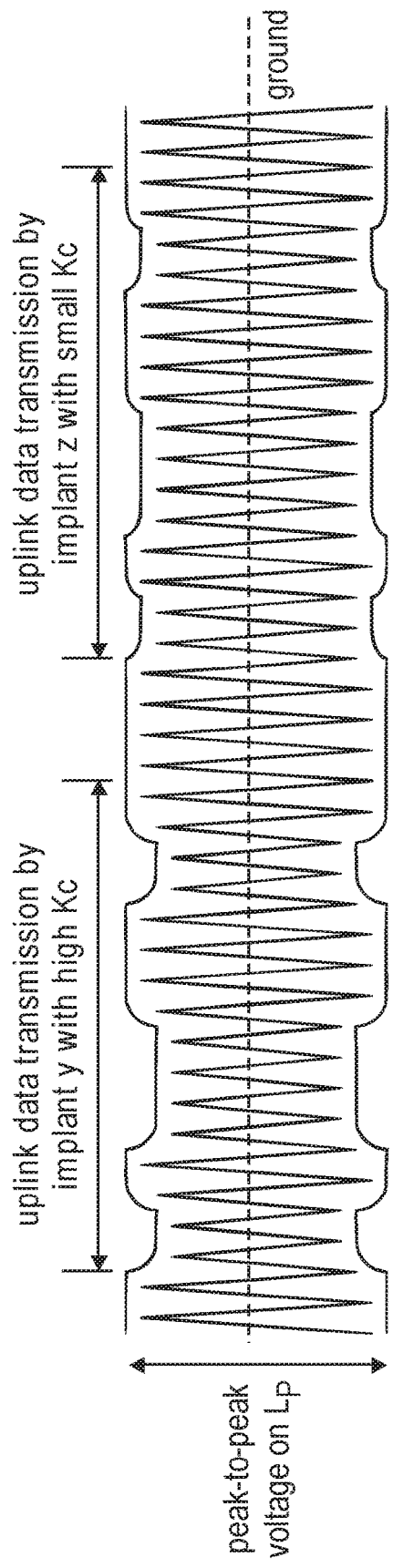
FIG. 2 is a diagram of a primary carrier signal on a primary coil of the telemetry controller that has been modulated in accordance with an amplitude shift keying (ASK) technique with uplink data received from the medical devices of FIG. 1.
Figure 3A:
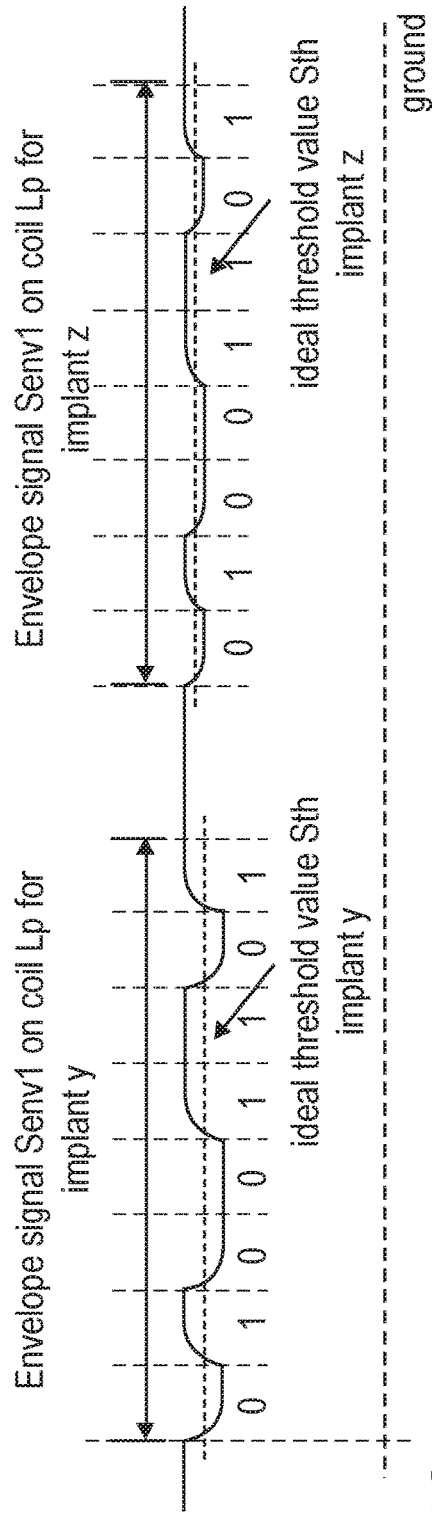
FIG. 3a is a diagram of an envelope signal detected from the modulated primary carrier signal of FIG. 2.
Figure 3B:
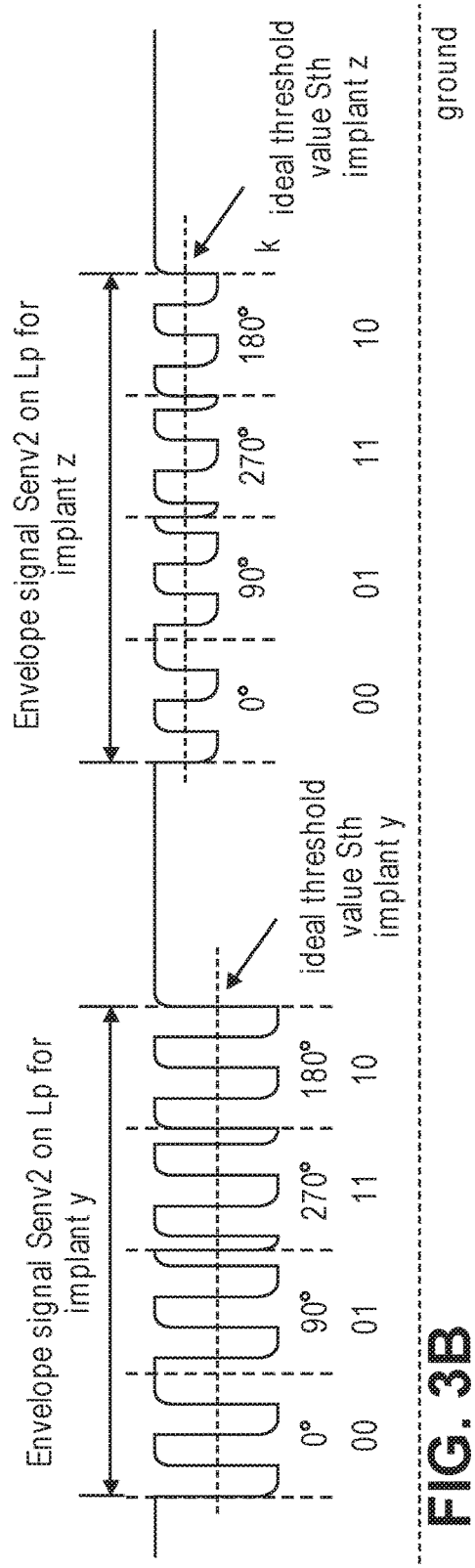
FIG. 3b is a diagram of an envelope signal alternatively detected from a primary carrier signal that has been modulated in accordance with a phase shift keying (PSK) technique with uplink data received from the medical devices of FIG. 1.
Figure 3C:
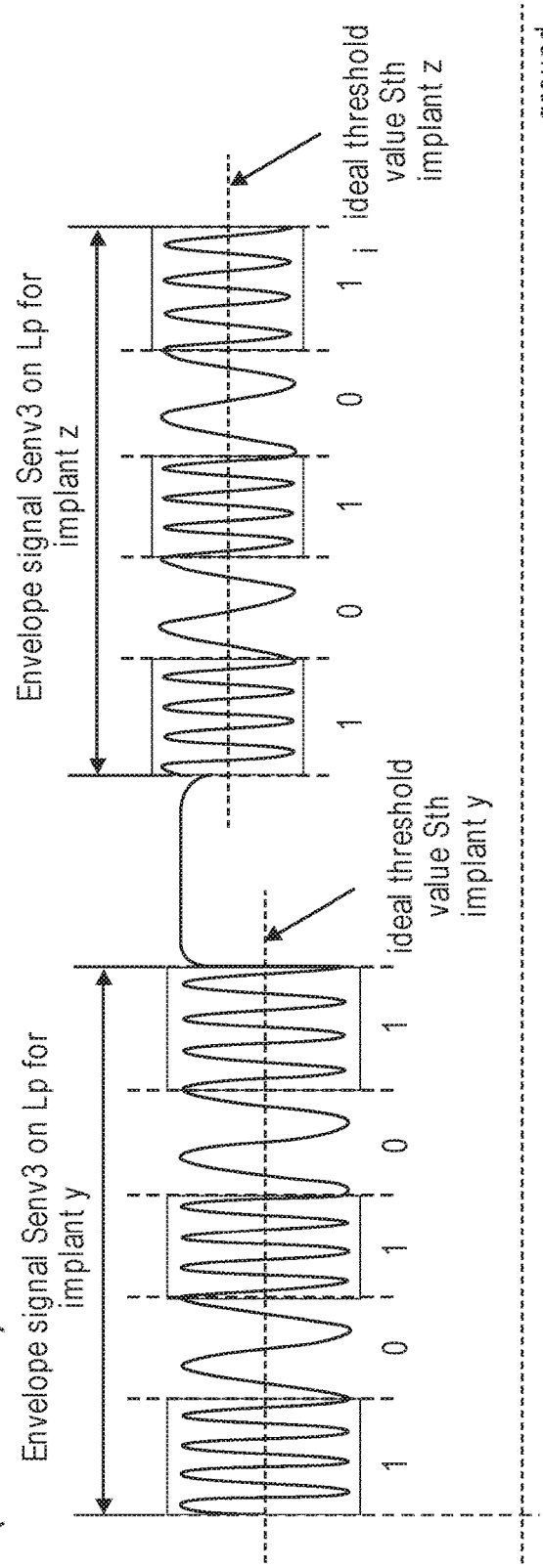
FIG. 3c is a diagram of an envelope signal alternatively detected from a primary carrier signal that has been modulated in accordance with a frequency shift keying (FSK) technique with uplink data received from the medical devices of FIG. 1.
Figure 4:
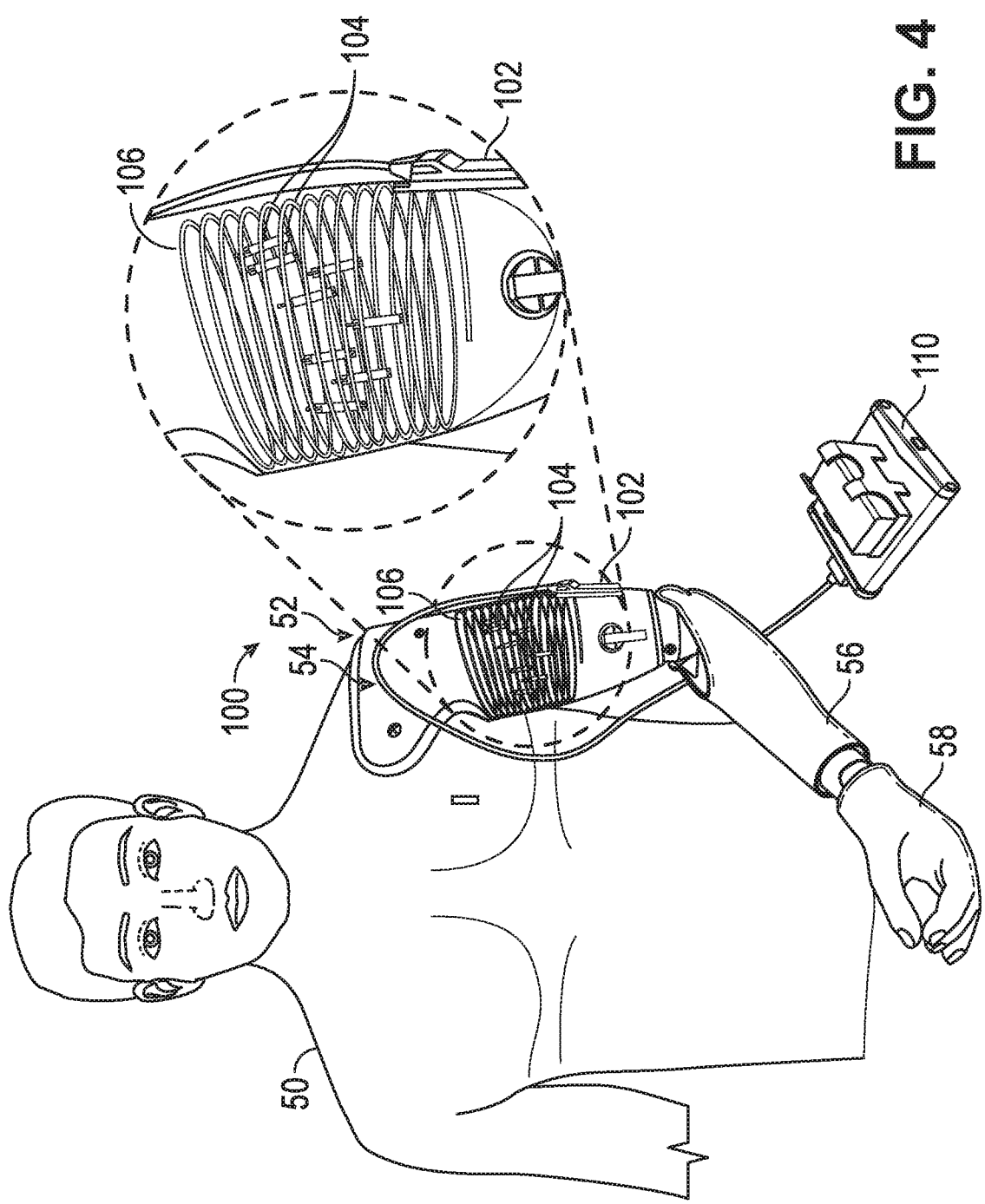
FIG. 4 is a pictorial of a prosthetic control system constructed in accordance with one embodiment of the present inventions.

Referring to FIG. 4, a medical system 100 constructed in accordance with one embodiment of the present inventions will now be described. The medical system 100 generally comprises an external telemetry controller (TC) 102 and a plurality of implantable medical devices 104. In the illustrated embodiment, the medical system 100 takes the form of a prosthetic control system.

In this case, the implantable medical devices 104 may take the form of sensor devices that are implanted within a residual portion of an amputated limb 52 of a patient 50 respectively adjacent muscles of interest for detecting muscle contraction, for example, by monitoring electromyogram (EMG) signals of the muscles of interest. The prosthetic control system 100 comprises a bionic prosthesis 54 having a prosthetic forearm 56 and prosthetic hand 58. The TC 102 may be incorporated into the bionic prosthesis 54, and is configured for delivering power to and receiving EMG data from the sensor devices 104. To facilitate power transfer and communications, the TC 102 comprises a primary coil 106, which may be incorporated into the socket portion of the bionic prosthesis 54 in a manner that it surrounds the sensor devices 104 implanted within the residual limb portion 52 of the patient 50. The TC 102 comprises power transfer and communication circuitry that inductively powers and communicates with the implanted sensor devices 104 via the primary coil 106.

The prosthetic control system 100 further comprises a prosthetic controller 110 coupled to the TC 102 via a cable 112 for receiving EMG data from TC 102, and is further coupled to motors (not shown) in the bionic prosthesis 54 to control movement of the prosthetic arm 56 and prosthetic hand 58. The prosthetic controller 110 may be worn by the patient 50, e.g., on the waist. The prosthetic control system 100 may further comprises one or more batteries (not shown), which may be physically integrated into the prosthesis 54 or otherwise contained in the prosthetic controller 110, for providing power to the circuitry within the TC 102 and prosthetic controller 110.

Thus, the prosthetic control system 100 allows the patient 50 to control the prosthetic forearm 56 and prosthetic hand 58 by attempting to contract the muscles in the residual limb portion 52. Different muscles or different portions of the muscles would correspond to independently movable parts, such as the elbow, wrist, and fingers of the bionic prosthesis 54. When a sensor device 104 detects contraction in a muscle or portion of a muscle, it communicates the resulting EMG data to the prosthetic controller 110 via the TC 102 that the muscle or portion of a muscle was contracted. The EMG data identifies the muscle that has been contracted, as well as the magnitude of the contraction. The prosthetic controller 110 then controls the bionic prosthesis 54 to move the independently movable part that corresponds with the muscle that was contracted according to the magnitude of the contraction.

Although the TC 102 and prosthetic controller 110 are shown as being separate physical units in FIG. 4, it should be appreciated that the TC 102 and prosthetic controller 110 may be integrated into a single physical unit that is incorporated into the prosthesis 54 or otherwise worn by the patient 50. It should also be appreciated that although the prosthetic control system 100 has been described as being a prosthetic control system, the prosthetic control system 100 can be any medical system that performs a diagnostic or therapeutic function. Likewise, although the implantable medical devices 102 are described as being EMG sensors, the implantable medical devices 102 may take the form of any medical device that performs a diagnostic or therapeutic function. Furthermore, although the TC 102 is described herein as being external to the patient 50, it should be appreciated that the TC 102 may take the form of, or otherwise be incorporated into, an implantable device that communicates with the other sensor devices 104.

In a conventional manner, the TC 102 may apply an exemplary unmodulated primary alternating current (AC) carrier signal Pcar to the primary coil 106, which induces exemplary unmodulated secondary AC carrier signals Scar1-Scarn on secondary coils 108 (shown in FIGS. 5a and 5b) of respective sensor devices 104(1)-104(n). The sensor devices 104(1)-104(n) may serially (one at a time) amplitude modulate the envelopes Senv1-Senvn of the secondary carrier signals Scar on the respective secondary coils 108 in accordance with data for transmission to the TC 102, thereby inducing an amplitude modulation of the envelope Penv of the primary carrier signal Pcar on the primary coil 106 that can be demodulated to acquire the data from the sensor devices 104. It should be appreciated that, for the purposes of this specification, "amplitude modulation" refers to any modulation where the peak-to-peak amplitude of a carrier signal is modified, and includes, e.g., such modulation techniques as AM, ASK, FSK, PSK, etc. In the specific embodiment illustrated herein, the sensor devices 104(1)-104(n) amplitude modulate secondary carrier signals on respective secondary coils using load modulation.

As discussed in the background, if the coupling coefficients Kc1-Kcn between the primary coil 106 and respective secondary coils 108 differ from each other, without compensation, the same load modulations applied to the secondary carrier signal envelopes Senv will induce different amplitude modulations on the primary carrier signal envelope Penv (i.e., the peak-to-peak amplitude of the primary carrier signal envelope Penv will be different for the sensor devices 104), which may require more complicated demodulation circuitry and/or slower data transmission rate to accurately acquire the data from the primary carrier signal Pcar.

Significantly, the prosthetic control system 100 is capable of equalizing the magnitude of the modulation of the primary carrier signal envelope Penv on the primary coil 106 of the TC 102 amongst the sensor devices 104 by load the secondary carrier signal envelopes Senv on the secondary coils 108, such that modulation magnitudes of the modulated secondary carrier signal envelopes Senv vary in an inversely varying relationship to the coupling coefficients Kc1-Kcn between the respective secondary coils 104(1)-104(n) and the primary coil 102. In other words, as a coupling coefficient Kc between the primary coil 106 and a particular secondary coil 108 increases, the modulation magnitude of the modulated secondary carrier signal envelope Senv on the secondary coil 108 is decreased, and conversely, as a coupling coefficient Kc between the primary coil 106 and a particular secondary coil 108 decreases, the modulation magnitude of the modulated secondary carrier signal envelope Senv on the secondary coil 108 is increased.

In order to select the proper modulation magnitudes for the secondary carrier signal envelopes Senv on the secondary coils 108, the prosthetic control system 100 indirectly measures the different coupling coefficients Kc1-Kcn between the primary coil 106 and the secondary coils 108 by measuring the amplitudes of the unmodulated secondary carrier signals across the respective secondary coils 108. That is, it is known that the amplitude of a secondary carrier signal induced on a secondary coil in response to the application of a primary carrier signal on a primary coil is proportional to the coupling coefficient between the primary coil and the secondary coil.

Figure 5A:
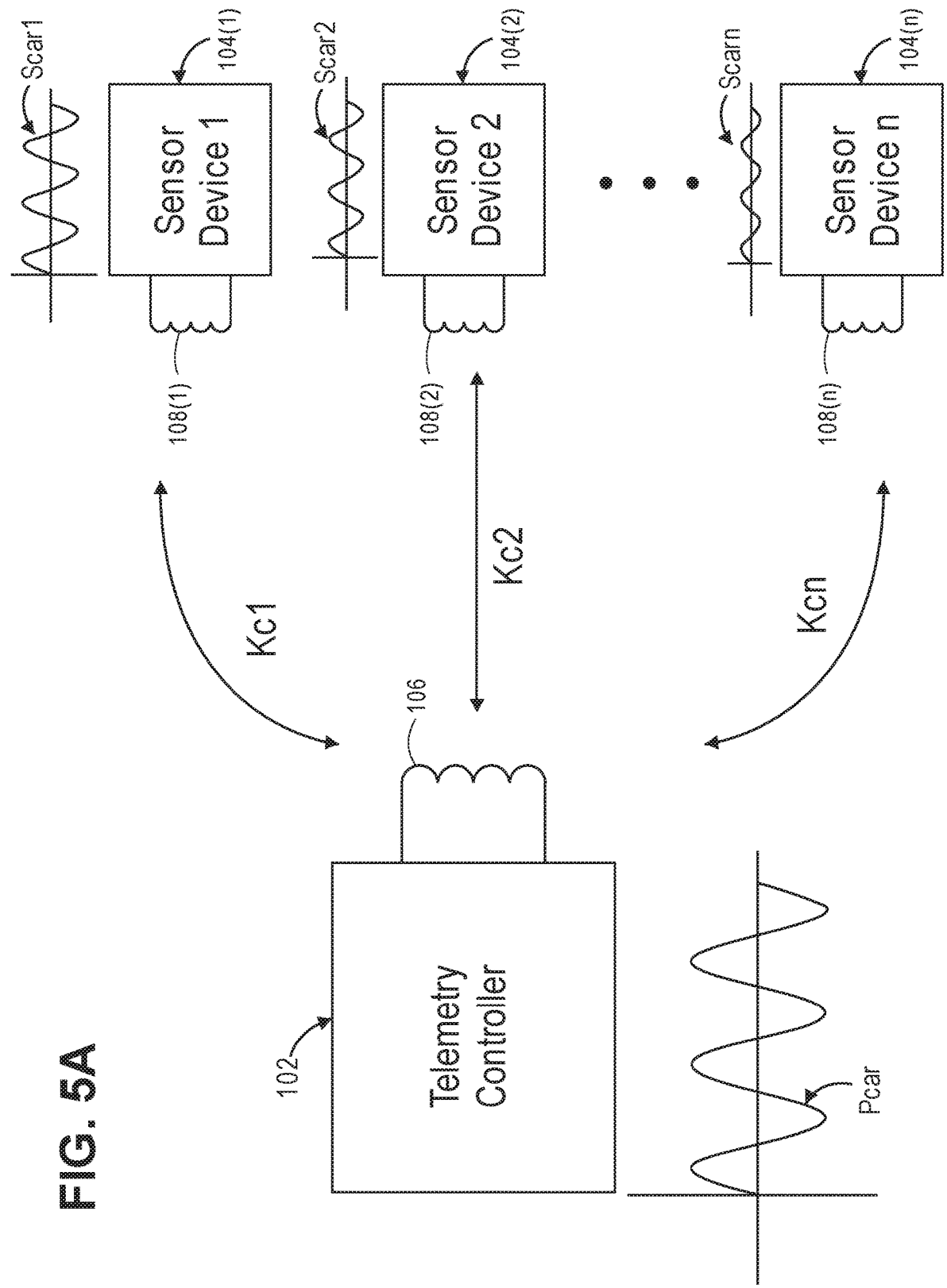
FIG. 5a is a block diagram of a telemetry controller and a plurality of sensor devices for use in the prosthetic control system of FIG. 4, particularly showing the induction of different secondary carrier signals on the secondary coils of the sensor devices in response to the application of a primary carrier signal on the primary coil of the telemetry controller.

For example, as shown in FIG. 5a, the peak-to-peak amplitudes of the respective secondary carrier signals on the secondary coils 108 will vary in accordance with the coupling coefficients Kc1-Kcn. That is, if the coupling coefficient Kc1 between the primary coil 106 and the secondary coil 108(1) is relatively high, the amplitude of the unmodulated secondary carrier signal on the secondary coil 108(1) will be relatively high; if the coupling coefficient Kc2 between the primary coil 106 and the secondary coil 108(2) is relatively medial, the amplitude of the unmodulated secondary carrier signal on the secondary coil 108(2) will be relatively medial; and if the coupling coefficient Kcn between the primary coil 106 and the secondary coil 108(n) is relatively low, the amplitude of the unmodulated secondary carrier signal on the secondary coil 108(n) will be relatively low.

Thus, the amplitude of the secondary carrier signal (preferably, unmodulated) on a secondary coil provides an accurate indication of the coupling coefficient between the primary coil and the secondary coil, and thus, can be used to select the modulation magnitude for the secondary carrier signal envelope Senv on that secondary coil. Thus, the modulation magnitude of the secondary carrier signal envelope Senv on any given secondary coil 108 will inversely vary with the measured amplitude of the unmodulated secondary carrier signal.

Figure 5B:
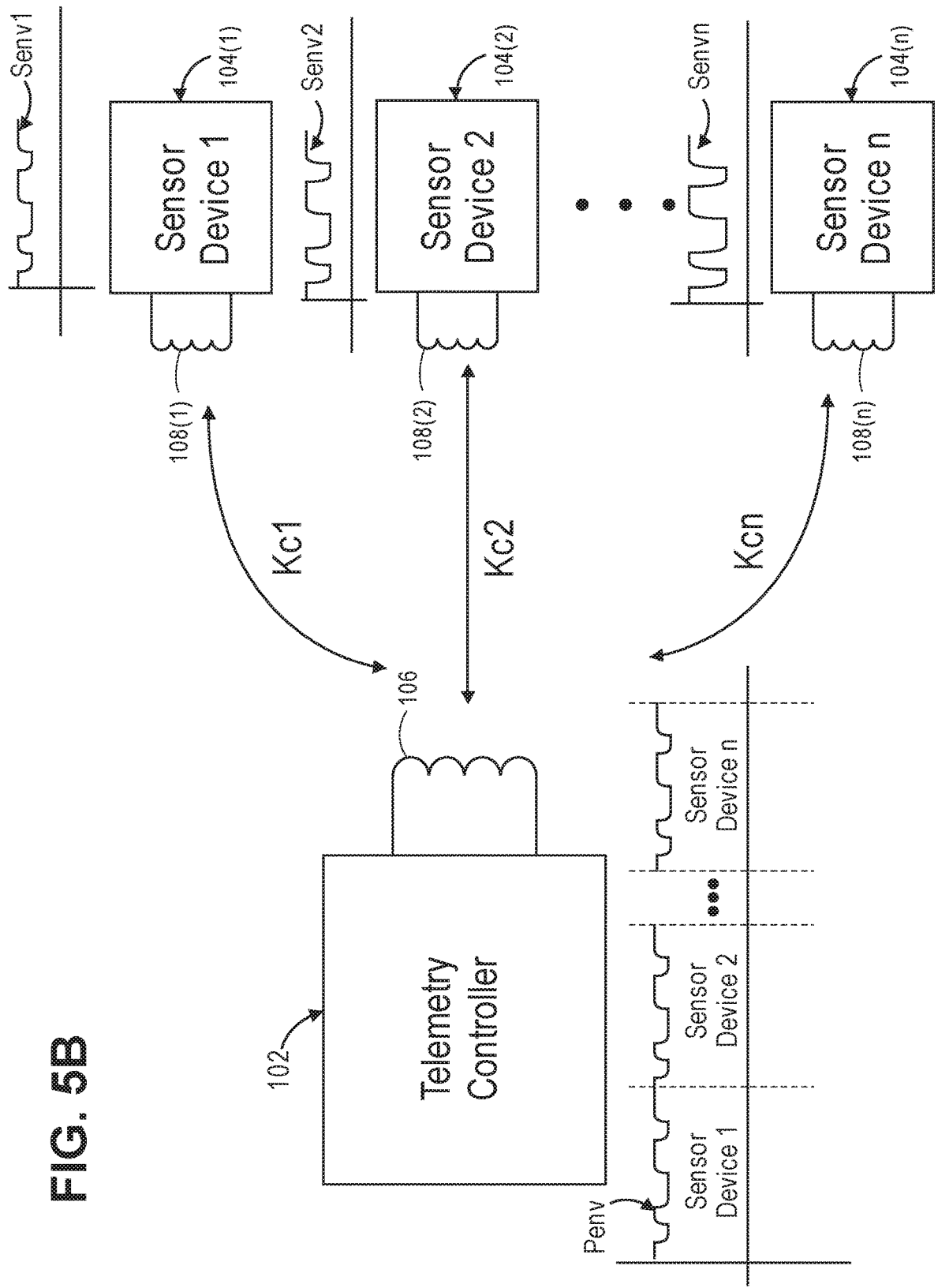
FIG. 5b is a block diagram of the telemetry controller and sensor devices of FIG. 5a, particularly showing the induction of amplitude modulations on the primary carrier signal on the primary coil of the telemetry coil in response to the application of amplitude modulations on the secondary coils of the respective sensor devices.

As shown in FIG. 5b, if the coupling coefficient Kc1 between the primary coil 106 and the secondary coil 108(1) is relatively high, the secondary carrier signal envelope Senv on the secondary coil 108(1) will be load modulated such that it has a relatively low modulation magnitude; if the coupling coefficient Kc2 between the primary coil 106 and the secondary coil 108(2) is relatively medial, the secondary carrier signal envelope Senv on the secondary coil 108(2) will be load modulated such that it has a relatively medial modulation magnitude; and if the coupling coefficient Kcn between the primary coil 106 and the secondary coil 108(2) is relatively low, the secondary carrier signal envelope Senv on the secondary coil 108(n) will be load modulated such that it has a relatively high modulation magnitude.

In this manner, variation of the modulation magnitude of the modulated primary carrier signal envelope Penv on the primary coil 106 between the sensor devices 104 will be decreased to compensate for the different coupling coefficients Kc1-Kcn (and secondarily, to compensate for any variation in tuning tolerances) between the primary coil 106 and the secondary coils 108. Preferably, the primary carrier signal envelope Penv is substantially uniformly amplitude modulated for the implanted sensor devices 104. For example, a variation in the modulation amplitude of the primary carrier signal envelope Penv between the implanted sensor devices 104 is less than 50%, and preferably less than 20%.

Figure 6:
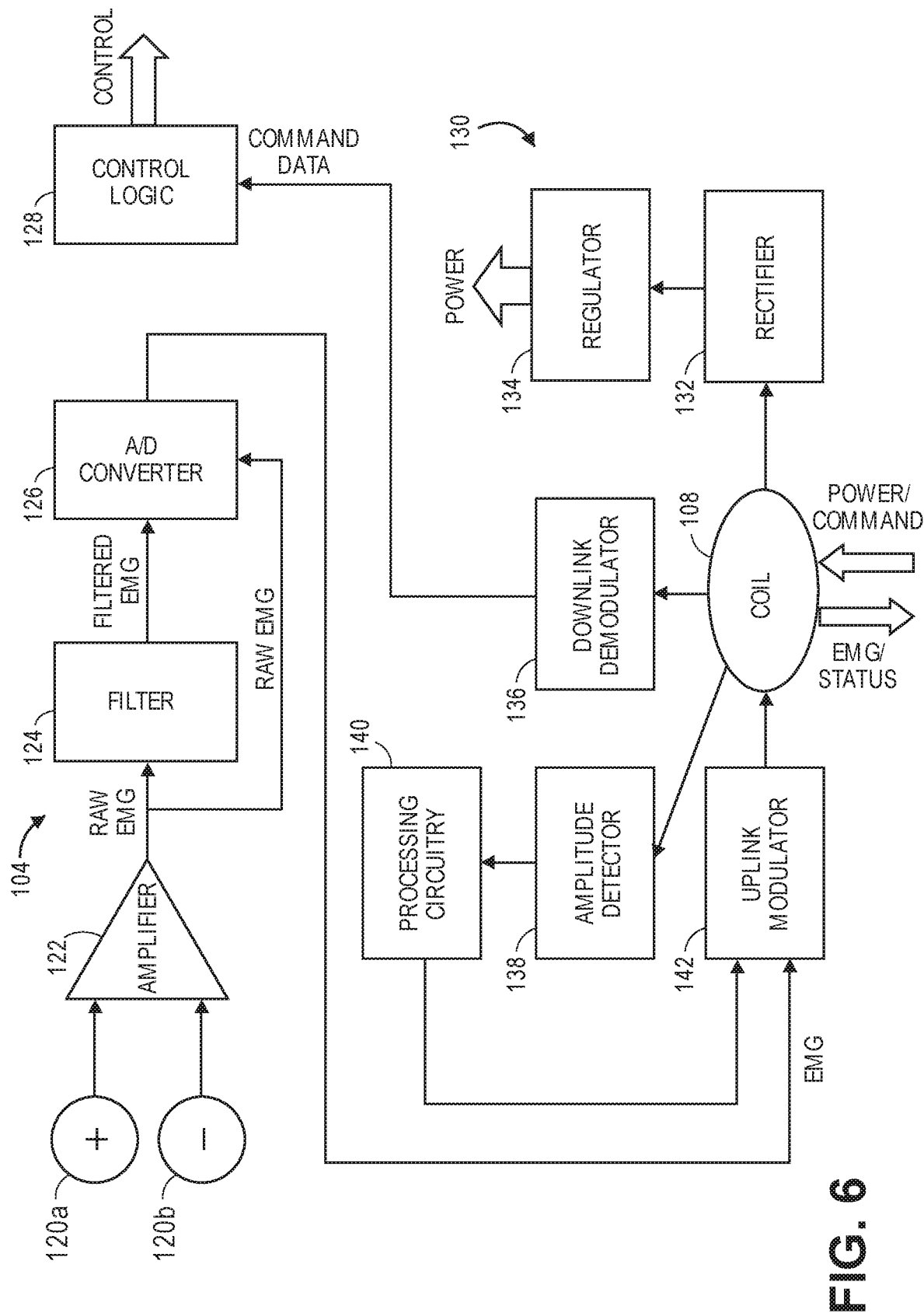
FIG. 6 is a block diagram of one of the sensor devices illustrated in FIGS. 5a and 5b.

Referring now to FIG. 6, each sensor device 104 is capable of sensing EMG signals. To this end, the sensor device 104 comprises two differential recording electrodes 120a, 120b configured for sensing electrical activity within the muscle fibers in which the sensor device 104 is implanted and outputting a raw analog EMG signal. In alternative embodiments, the sensor device 104 may sense electrical impedance, field potential, evoked potential from nerves, temperature, pressure, tension, translucence, reflectance, pH, motion, inertial, chemical, respiration, vascular pulsation, heartbeat, ECG, EKG, EEG, EOG, etc.

The sensor device 104 further comprises one or more adjustable gain amplifiers 122 configured for amplifying the EMG signal; a filter 124 configured for obtaining an envelope, integrating, or sampling the EMG signal; an analog-to-digital converter (A/D) converter 126 configured for selectively transforming either the raw EMG signal output from the amplifier(s) 122 or the filtered EMG signal output from the filter 124 into a digitized EMG signal; and control logic 128 (e.g., command processor, frame generator, PLL logic, command decoder, and error correction circuitry) configured for controlling and operating the sensor device 104 in accordance with commands received from the TC 102. The filter 124 can also be realized digitally. In this case, the filter 124 would be placed after the A/D converter 126.

The sensor device 104 further comprises telemetry/power circuitry 130 configured for receiving commands and power from the TC 102 and transmitting the EMG signal (either raw or filtered) to the TC 102. In the illustrated embodiment, the sensor device 104 utilizes a robust half-duplex data link for transmitting the filtered or raw EMG signal to the TC 102 and receiving command data from the TC 102.

To this end, the telemetry/power circuitry 130 comprises the aforementioned secondary coil 108 on which the secondary carrier signal is induced in response to the application of the primary carrier signal on the primary coil 106 of the TC 102. The telemetry/power circuitry 130 utilizes secondary carrier signal as both a source of power and as a downlink/uplink carrier signal. The telemetry/power circuitry 130 further comprises a rectifier 132 and power regulator 134 for rectifying and regulating the inductive carrier signal received at the secondary coil 108 for powering the circuitry of the sensor device 104. In alternative embodiments, the sensor device 104 may include a rechargeable battery (not shown) for storing the electrical energy, or a non-rechargeable battery, in which case, power may be supplied to the circuitry of the sensor device 104 without connection to the TC 102. In this case, the sensor device 104 may further comprise memory (not shown) for storing the EMG data that can be subsequently transmitted via a dedicated communication coil upon interrogation of the sensor device 104 by the TC 102.

The telemetry/power circuitry 130 further comprises a downlink inductive demodulator 136 configured for demodulating command data received from the TC 102 from the secondary carrier signal at the secondary coil 108. In the illustrated embodiment, the downlink inductive demodulator 136 is an amplitude modulation (AM) demodulator that demodulates the downlink data by measuring the amplitude variations of the secondary carrier signal.

More significant to the present inventions, the telemetry/power circuitry 130 comprises an amplitude detector 138 configured for measuring the amplitude of the secondary carrier signal. In the illustrated embodiment, the amplitude detector 138 is configured for measuring a peak amplitude of the secondary carrier signal, although in alternative embodiments, the amplitude detector 138 may, e.g., measure a root mean square (RMS) amplitude of the secondary carrier signal. The telemetry/power circuitry 130 further comprises processing circuitry 140 configured for selecting a magnitude of a load modulation of the secondary carrier signal at the secondary coil 108 in accordance with an inversely varying relationship with the measured amplitude of the secondary carrier signal. That is, the greater the measured amplitude of the secondary carrier signal, the less the selected modulation magnitude of the secondary carrier signal, and the less the measured amplitude of the secondary carrier signal, the greater the selected modulation magnitude of the secondary carrier signal.

Figure 7A:
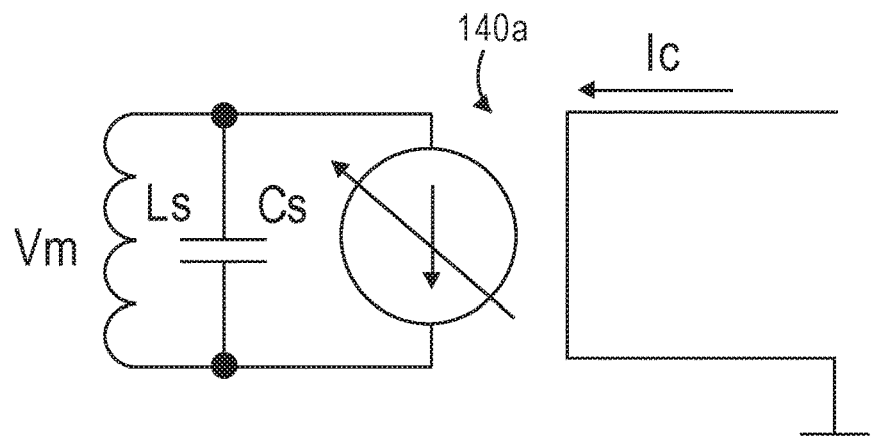
FIG. 7a is a schematic illustrating one embodiment of processing circuitry used to generate a modulation current for load modulating the secondary carrier signal on the secondary coil of the sensor device of FIG. 6 by varying the loading current on the secondary coil Ls.
Figure 7B:
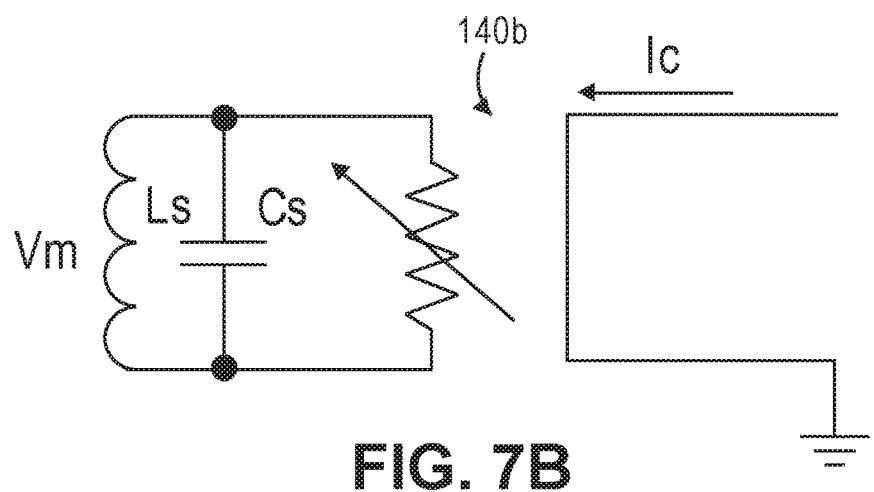
FIG. 7b is a schematic illustrating another embodiment of processing circuitry used to generate a modulation current for load modulating the secondary carrier signal on the secondary coil of the sensor device of FIG. 6 by varying the loading resistance on the secondary coil Ls.
Figure 7C:
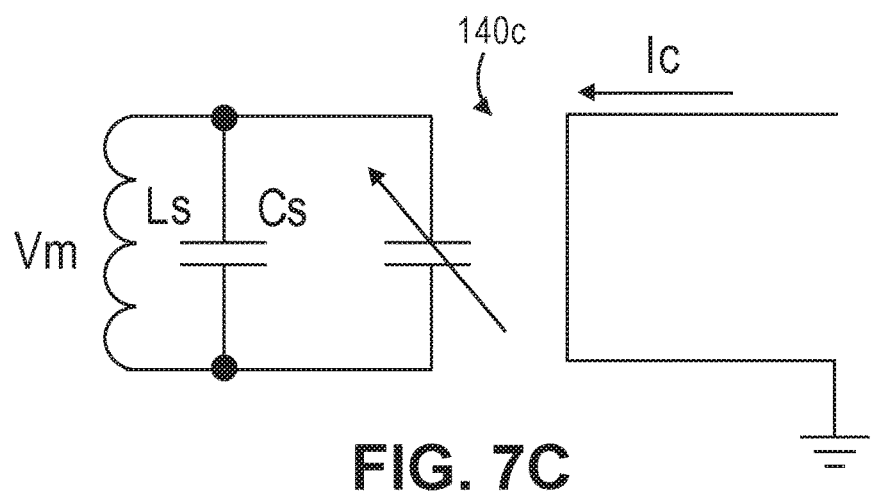
FIG. 7c is a schematic illustrating still another embodiment of processing circuitry used to generate a modulation current for load modulating the secondary carrier signal on the secondary coil of the sensor device of FIG. 6 by varying the equivalent capacitance of the capacitor Cs.

In the illustrated embodiment, the processing circuitry 140 may, e.g., select the modulation magnitude via a current-controlled variable current source 140a, as illustrated in FIG. 7a. The current-controlled variable current source 140a is controlled via a modulating current Ic, such that a modulation voltage Vm (i.e., a change in the voltage across the secondary coil Ls) is selected. As the current output of the variable current source 140a increases, the modulation voltage Vm increases. Alternatively, the processing circuitry 140 may, e.g., select the modulation magnitude via a current-controlled variable resistor 140b, as illustrated in FIG. 7b. The variable resistor 140b is controlled via a modulating current Ic, such that the modulation voltage Vm is selected. As the resistance of the variable resistor 140b decreases, the modulation voltage Vm increases. Alternatively, the processing circuitry 140 may, e.g., select the modulation magnitude via a current-controlled variable capacitor 140c, as illustrated in FIG. 7c. The variable capacitor 140c is controlled via a modulating current Ic, such that the modulation voltage Vm is selected. As the capacitance of the variable capacitor 140c increases, the modulation voltage Vm increases. Although the processing circuitry 140 utilizes a current input Ic as the control signal to control the variable current source 140a in FIG. 7a, the variable resistor 140b in FIG. 7b, or the variable capacitor 140c in FIG. 7c, it should be appreciated that the processing circuitry 140 may alternatively utilize a control voltage to control the variable current source 140a, variable resistor 140b, or variable capacitor 140c.

Referring back to FIG. 6, the telemetry/power circuitry 130 further comprises an uplink modulator 142 configured for applying the selected modulation magnitude to the secondary carrier signal at the secondary coil 108 in accordance with the raw or filtered EMG received from the A/D converter 126, thereby inducing an amplitude modulation of the primary carrier signal envelope on the primary coil 106. In optional embodiments, operational status data can be transmitted by the sensor device 104 to the external control unit 16 via the secondary coil 108 to provide, for example, battery status information or other operational information of the sensor device 104, in which case, the uplink modulator 142 may be configured for applying the selected modulation magnitude to the secondary carrier signal at the secondary coil 108 in accordance with the operational status data. In the alternative case wherein the implantable medical device is a therapeutic device, such as a neurostimulator, the operational status data may be include electrical measurements made by the neurostimulator while stimulating a neuromuscular pathway.

The sensor device 104 may take the form of a miniaturized cylindrical sensing device, with the circuitry being implemented as a sub-assembly on a single-chip integrated circuit mounted on a ceramic substrate sandwiched between two halves of a cylindrical magnetic core around which the inductive coil is wound. The electronics are encapsulated in a cylindrical ceramic package that include two metal end-caps at opposite ends of the ceramic package that serve as the differential recording electrodes. Such an implantable sensor device allows the EMG signals to be detected at the implantation site of this device. An example of such an implantable sensor device 104 is the IMES® device manufactured by The Alfred Mann Foundation for Scientific Research and described in Implantable Myoelectric Sensors (IMESs) for Intramuscular Electromyogram Recording, IEEE Trans Biomed Eng., 2009, January, pp. 159-171. In an alternative embodiment, the sensor device 104 may include a lead (not shown) on which the electrodes are carried, so that EMG signals can be detected at a location remote from the implantation site of the body of the device.

Figure 8:
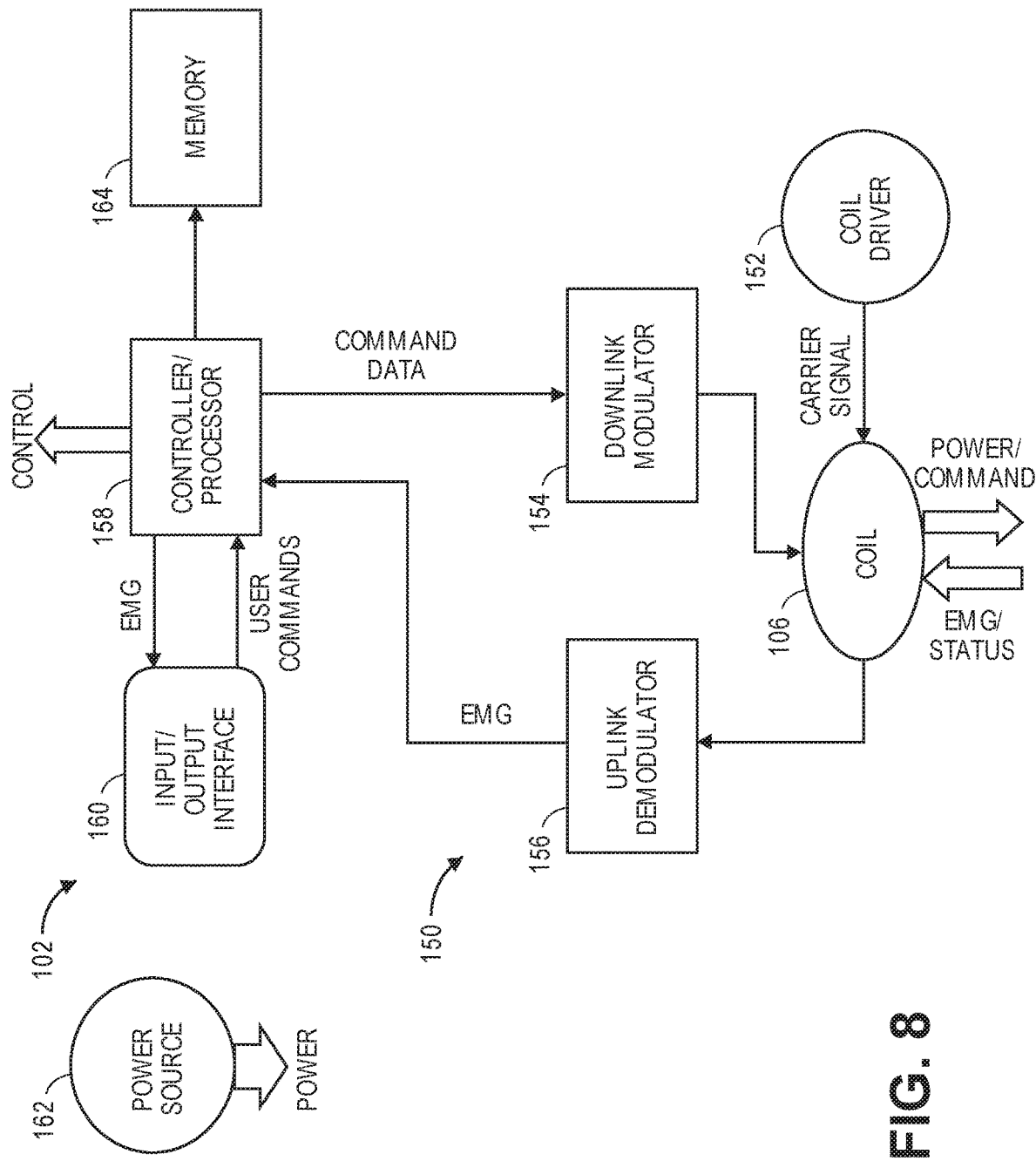
FIG. 8 is a block diagram of the telemetry controller illustrated in FIGS. 5a and 5b.

Referring to FIG. 8, the TC 102 comprises telemetry/power circuitry 150 configured for transmitting commands and power to the sensor devices 104 and receiving the EMG signal (either raw or filtered), or status signals, from the sensor devices 104. To this end, the telemetry/power circuitry 150 comprises the aforementioned primary coil 106 and a coil driver 152 configured for applying the primary carrier signal to the primary coil 106, thereby inducing the secondary carrier signals on the secondary coils 108 of the sensor devices 104.

As described above, the primary carrier signal is utilized as both a source of power and as a downlink/uplink carrier signal. To this end, the telemetry/power circuitry 150 further comprises a downlink modulator 154 configured for modulating the primary carrier signal with command data by varying the carrier signal at the primary coil 106 in accordance with the command data. Like the uplink modulator 142 in each of the sensor devices 104, the downlink modulator 154 is an amplitude modulator that modulates the amplitude of the primary carrier signal, thereby allowing the sensor device 104 to acquire the command data as described above. The telemetry/power circuitry 150 further comprises an uplink demodulator 156 configured for demodulating the primary signal envelope at the primary coil 106 to acquire the EMG data (or status data) from the sensor devices 104. The uplink demodulator 156 may acquire the EMG data from the primary carrier signal in a conventional manner by first detecting the modulated primary carrier signal envelope, and then comparing the detected envelope of the primary carrier signal to a threshold level that is preferably centered between a minimum and a maximum of the modulated primary carrier signal envelope.

Figure 9A:
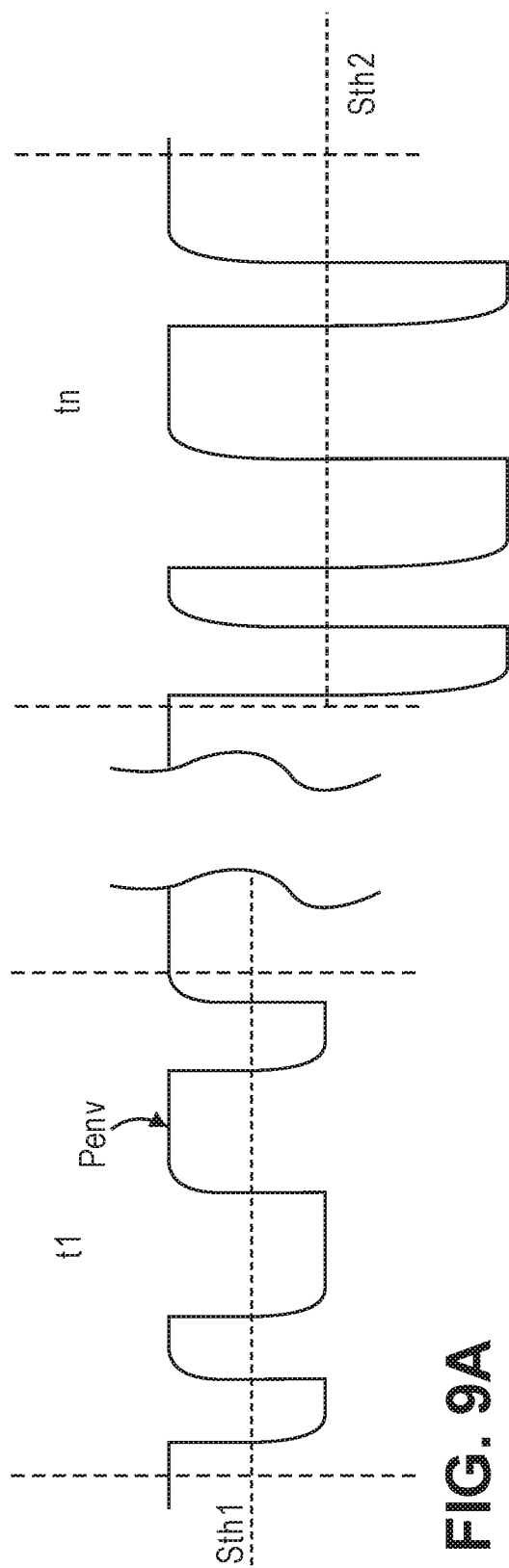
FIG. 9a is a diagram of a primary carrier signal on a primary coil of a prior art telemetry controller, particularly showing a non-uniform modulation of the primary carrier signal induced by the modulation of secondary carrier signals on the secondary coils of sensor devices.
Figure 9B:
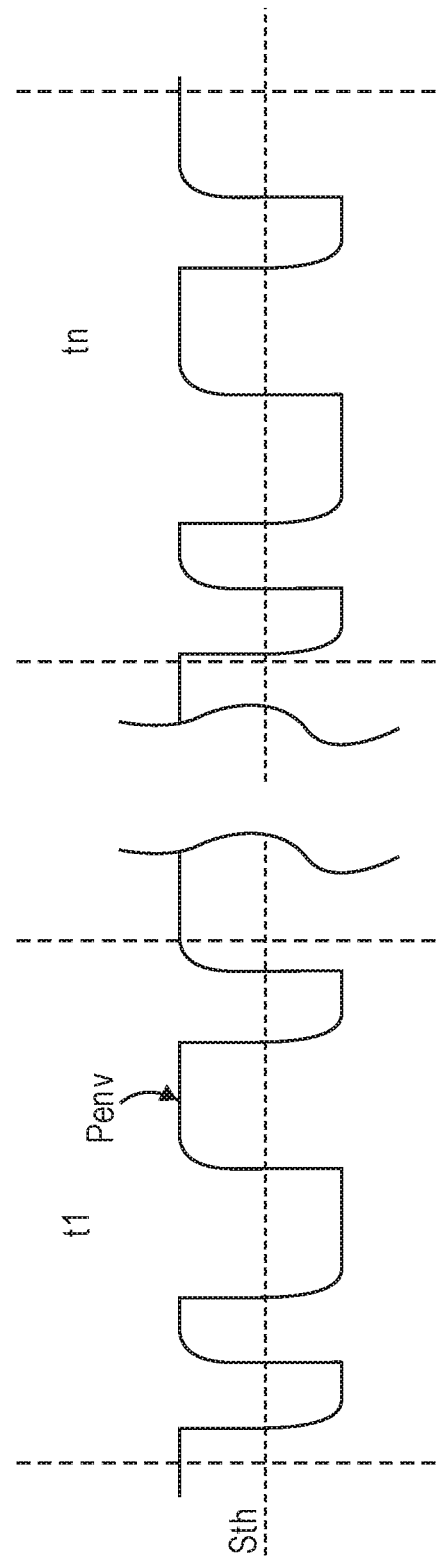
FIG. 9b is a diagram of a primary carrier signal on the primary coil of the telemetry controller of FIG. 8, particularly showing a uniform modulation of the primary carrier signal induced by the modulation of secondary carrier signals on the secondary coils of the sensor devices of FIGS. 5a and 5b.

For example, as shown in FIGS. 9a and 9b, the data (e.g., EMG data) can be serially received from the sensor devices 104(1)-104(n) in an n number of dedicated time slots, respectively. As shown in FIG. 9a, without using the aforementioned compensation technique, the primary carrier signal envelope Penv is not uniformly modulated for the sensor devices 104 over time slots t1-tn, such that multiple threshold levels Sth1-Sthn must be used to acquire the data from the primary carrier signal envelope Penv. However, as shown in FIG. 9b, using the aforementioned compensation technique, the primary carrier signal envelope is substantially uniformly amplitude modulated for the sensors devices 104 over time slots t1-tn, such that a single threshold level Sth may be used. As the primary carrier signal envelope crosses the threshold level Sth in one direction, a "1" or a "0" is detected (depending on the coding scheme), and as the primary carrier signal envelope crosses the threshold level Sth in the other direction, a "0" or a "1" is detected. Thus, it can be appreciated that the demodulator 156 may utilize a simple comparator with a fixed threshold level to detect the uplink data. Although the primary carrier signal envelope is described as being amplitude modulated in accordance with an amplitude shift keying (ASK) technique, it should be appreciated that the primary carrier signal envelope may be amplitude modulated in accordance with other techniques, such as phase shift keying (PSK) and frequency shift keying (FSK) techniques.

The TC 102 further comprising a controller/processor 158 configured for controlling and operating the TC 102, and processing the EMG data (raw or filtered) received from the sensor device 104. The TC 102 further comprises an input/output interface 160, such as a USB port, for communicating the processed EMG data to, and receiving commands, from the prosthetic controller 110 via the cable 112 (shown in FIG. 4). The TC 102 further comprises a power source 162, e.g., a battery, for providing power to the circuitry of the TC 102, and memory 164 configured for storing information, such as EMG data.

Figure 10:
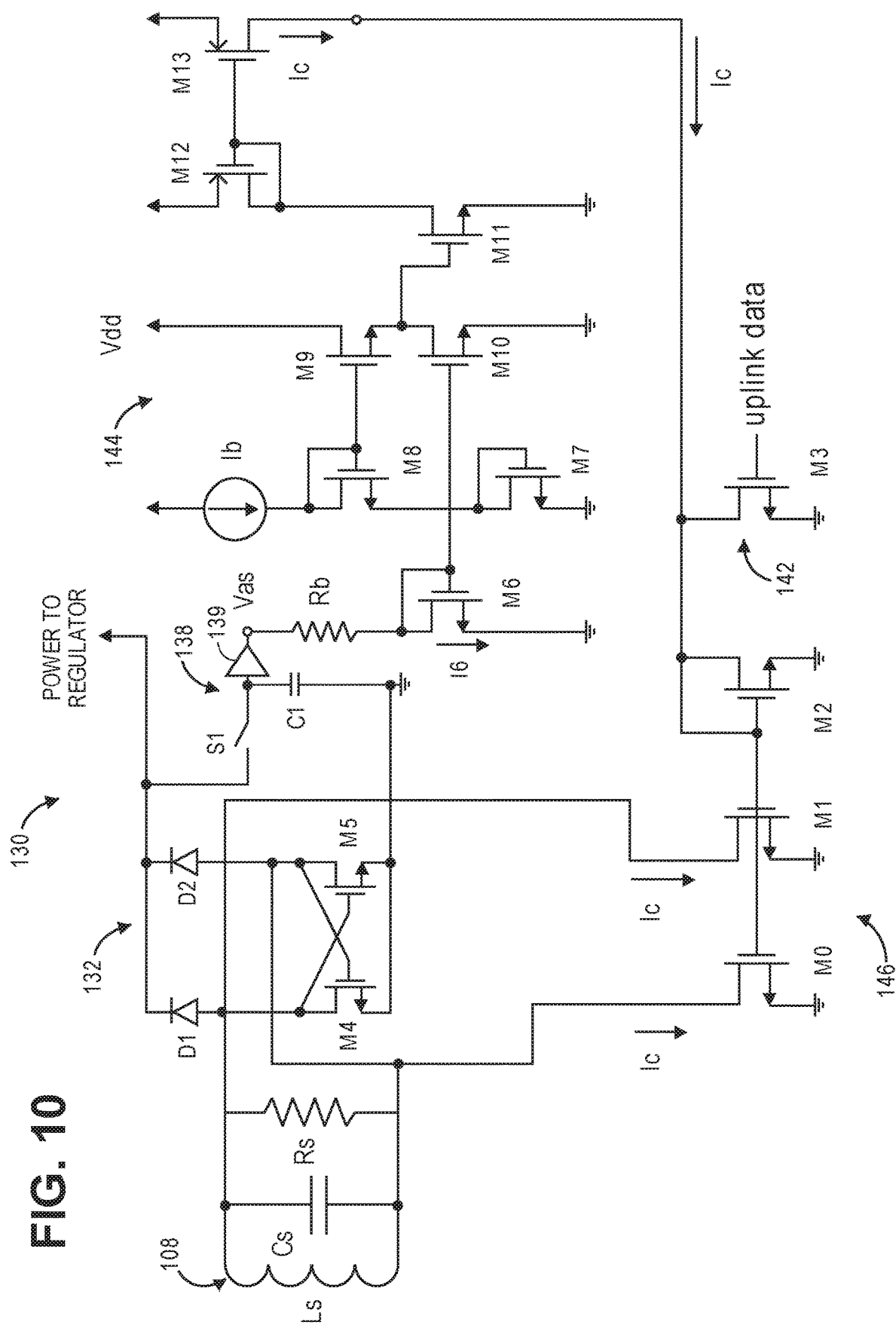
FIG. 10 is a schematic of telemetry/power circuitry of the sensor device of FIG. 6.

Referring now to FIG. 10, a detailed implementation of the telemetry/power circuitry 130 of the sensor device 104 will be described. In a conventional manner, the secondary coil 108 is represented by inductance Ls, and is combined in parallel with a capacitance Cs to form a receiver LC tank circuit that is inductively linked to corresponding transmitter LC tank circuit comprising the primary coil 106 and capacitance (not shown) at the TC 102. The receiver LC tank circuit and transmitter LC tank circuit are tuned to resonant at the frequency of the carrier signal generated by the TC 102, such that there is no parasitic reaction between the respective LC tank circuits.

The rectifier 132 is a conventional diode rectifier with cross-coupled NMOS transistors coupled across the receiver LC tank circuit to rectify the secondary carrier signal, and that delivers the rectified carrier signal to the regulator 134 for powering the circuitry. The positive portion of the secondary carrier signal is conducted through diode D1 to the regulator 134, while reverse biasing diode D1 via transistor M5, and the negative portion of the secondary carrier signal is conducted through diode D2 to the regulator 134, while reverse biasing diode D2 via transistor M4.

The amplitude detector 138 is coupled to the output of the rectifier 132 and includes a capacitor C1 for detecting the peak amplitude of the rectified secondary carrier signal across the secondary coil 108, and in this case, the amplitude of the unmodulated voltage Vas across the secondary coil 108 of the secondary carrier signal. The amplitude detector 138 is provided with a switch S1 that can be opened or closed to selectively detect or not detect the unmodulated voltage amplitude Vas across the secondary coil 108. The amplitude detector 138 is provided with a voltage buffer 139 for buffering the unmodulated voltage amplitude stored on the capacitor C1 as Vas.

The processing circuitry 140 selects a modulating current Ic (which in the illustrated embodiment, is equivalent to a change in the load current $\Delta I_L$) through the secondary coil 108 as a function of the measured unmodulated voltage Vas across the secondary coil 108 and stored in the voltage buffer 139, such that the modulated envelope voltage Venv of the primary carrier signal on the primary coil 106 is substantially uniform for all of the sensor devices 104 communicating with the TC 102. To this end, the processing circuitry 140 comprises a voltage-to-current converting circuit 144 configured for applying a dynamic function to the detected voltage Vas to output a modulating current Ic. The voltage-to-current converting circuit 144 may be a conventional circuit known to provide a dynamic inverting function (i.e., as the input voltage increases, the output current decreases, and as the input voltage decreases, the output current increases), such as the function shown in FIG. 11. The voltage-to-current converting circuit 144 comprises a resistor Rb, which converts the unmodulated voltage amplitude Vas into the drain current I6 of transistor M6. The voltage-to-current converting circuit 144 will produce an output current Ic, which is equal to K·Ib/I6, where K is a constant and $I_B$ is a bias current inside the voltage-to-current converting circuit 144. A supply voltage of Vdd is used to power the voltage-to-current converting circuit 144. It should be appreciated that, although the voltage-to-current converting circuit 144 has been described as being analog in nature, the voltage-to-current converting circuit may be digital in nature. In this case, an analog-to-digital (A/D) converter can transform the analog detected voltage Vas to a digital voltage prior to input into the voltage-to-current converting circuit 144, and a digital-to-analog (D/A) converter can transform the digital modulating current Ic into an analog current. A look-up table of voltage values and corresponding current values according to a dynamic inverting function, such as that shown in FIG. 11, can be stored in memory (not shown) as part of the digital voltage-to-current converting circuit 144, which can be accessed by a digital processor.

The processing circuitry 140 further comprises current mirror circuitry 146 configured for applying the modulating current Ic output by the voltage-to-current converting circuit 144 to the secondary coil 108, subject to the output of the modulator 142, which takes the form of transistor M3. In particular, the current mirror circuitry 146 comprises a current mirror M2-M1 coupled to the positive terminal of the secondary coil 104, and a current mirror M2-M0 coupled to the negative terminal of the secondary coil 104.

Thus, when the transistor M3 is switched off in response to an input of a particular bit value (e.g., a binary "1") from the uplink data stream, the modulating current Ic is passed through to the current mirror M2-M1, which mirrors the modulating current Ic to the positive terminal of the secondary coil 108, resulting in a decrease in the positively polarized envelope of the voltage across the secondary coil 104, as well as is passed through the current mirror M2-M0, which mirrors the modulating current Ic to the negative terminal of the secondary coil 108, resulting in an increase in the negatively polarized envelope of the voltage across the secondary coil 104. As a result, the voltage envelope Venv at the primary coil 104 is "low," indicating the particular bit value of "1." In contrast, when the transistor $M_3$ is switched on in response to an input of the other bit value (e.g., a binary "0") from the uplink data stream, the modulating current Ic is grounded through the transistor M3, and is therefore not passed through to the current mirrors M2-M1 and M2-M0, resulting in no change to the positively polarized envelope or negatively polarized envelope of the voltage across the secondary coil 104. As a result, the voltage envelope Venv at the primary coil 104 is "high," indicating the particular bit value of "0."

It should be noted that the voltage envelope Venv at the primary coil 104 can be made to be uniform without direct knowledge of the coupling coefficients Kc by defining the function between unmodulated voltage Vas and the modulating load current $\Delta I_L$ that achieves the uniform voltage envelope Venv. As an initial matter, for a fixed primary carrier signal applied to the primary coil 106, as well as for fixed values for Ls, Cs, and Rs inside the sensor device 104, the unmodulated voltage Vas across the secondary coil 108 only depends upon, and is typically proportional to, the coupling coefficient Kc between the primary coil 106 and that secondary coil 108. Since the envelope voltage Venv on the primary coil 106 depends on the coupling coefficient Kc and a modulating current Ic (e.g., a current through the secondary coil 108), the envelope voltage Venv is a function of the coupling coefficient Kc and the modulating current Ic, and can be given as Venv=f(Kc, Ic). Assume that the function f(Kc, Ic) is separable and can be written as g(Kc)·h(Ic). Then, since the unmodulated voltage Vas across the secondary coil 108 is related to the coupling coefficient Kc, the envelope voltage Venv on the primary coil 108 can be further written as Venv=G(Vas)·h(Ic) by replacing the function g(Kc) with the function G(Vas). To have a constant envelope voltage Venv on the primary coil 108 independent of the coupling coefficient Kc (and hence, the unmodulated voltage Vas across the secondary coil 108, the function of h(Ic) should be made proportional to the inverse of the function G(Vas), given as $G^{-1}$(Vas) with the modulating current Ic being a function of the unmodulated voltage Vas on the secondary coil 108, given as Ic=x(Vas). Therefore, the envelope voltage Venv on the primary coil 108 can be written as:

$$Venv = g(Kc) \cdot h(Ic) = G(Vas) \cdot h(Ic) = G(Vas) \cdot G^{-1}(Vas) = G(Vas) \cdot h(x(Vas)),$$

where Ic=x(Vas).

With this in mind, sensor devices 104 can be manufactured in a manner, such that the modulated signal envelope Senv on the primary coil 108 during uplink communication is substantially uniform across all of the sensor devices 104. As a significant part of this manufacturing process, the dynamic inverting function illustrated in FIG. 11 can be customized to the specific primary coil 106 and secondary coil 108 of the respective telemetry controller 102 and sensor device 104 to be manufactured, so that the sensor devices 104 can load modulate the secondary carrier signals on the respective secondary coils 108 that more accurately results in a substantially uniform modulated signal envelope Senv on the primary coil 108.

Figure 12:
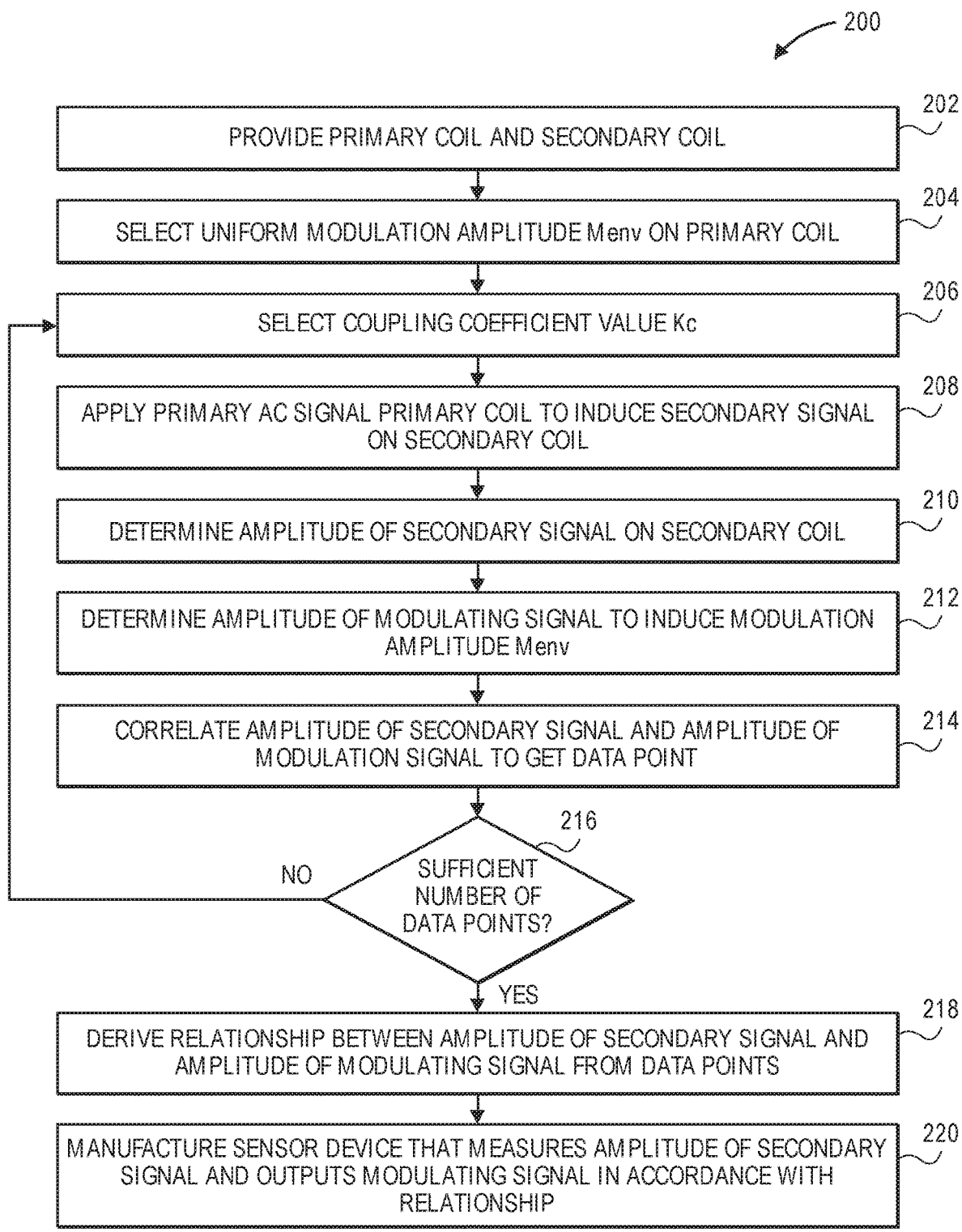
FIG. 12 is a flow diagram illustrating one method of manufacturing the sensor device of FIGS. 5a and 5b.

For example, one method 200 of manufacturing the sensor device 104 will be described with respect to FIG. 12. First, the primary coil Lp and the secondary coil Ls, respectively corresponding to the primary coil 106 that will be used in the telemetry controller 102 and the secondary coil 108 that will be used in each of the sensor devices 104, are provided (step 202). Actual versions of the primary coil Lp and the secondary coil Ls may be provided, or alternatively, the primary coil Lp and the secondary coil Ls may be simulated. Next, a uniform value (e.g., a uniform voltage value Menv) for an amplitude modulation induced on the primary coil Lp is selected (step 204). In the illustrated embodiment, the uniform value for the amplitude modulation induced on the primary coil Lp is selected to be the minimum value expected between the corresponding primary coil 106 and secondary coil 108, assuming the worst-case functioning coupling coefficient Kc. Next, a coupling coefficient value Kc is selected between the primary coil Lp and the secondary coil Ls (step 206). In the illustrated embodiment, the expected worst-case value of the coupling coefficient Kc is selected.

Next, a primary alternating current (AC) signal having a fixed value (e.g., fixed current value) is applied to the primary coil Lp, thereby respectively inducing a secondary signal on the secondary coil Ls for the coupling coefficient value Kc (step 208). The amplitude of the secondary signal (e.g., the peak voltage amplitude) is then determined (step 210). Next, the amplitude of a modulating signal (e.g., a signal that defines a change in the current within the secondary coil 208) for modulating an envelope of the secondary signal is determined, such that it induces an amplitude modulation on the primary coil Lp that is substantially equal to the uniform amplitude modulation value selected in step 202 (step 212). In one method, the amplitude of the modulating signal is determined by adjusting the modulating signal until the amplitude modulation induced on the primary coil Lp is substantially equal to the selected uniform amplitude modulation value. It should be appreciated that steps 208-212 can be performed in an actual environment, in which case, the amplitude of the secondary signal on the secondary coil Ls at step 210 and the amplitude modulation on the primary coil Lp at step 212 can be measured, or steps 218-212 can be performed in a simulated environment, in which case, the amplitude of the secondary signal on the secondary coil Ls at step 210 and the amplitude modulation on the primary coil Lp at step 212 can be computed.

Next, the determined amplitudes of the secondary signal and modulating signal are correlated to create a data point (step 214), and steps 206-214 are repeated for different coupling coefficient values using the same fixed value for the primary signal that is applied to the primary coil Lp, as well as the same values for the inductance Ls, capacitance Cs, and load resistance Rs, thereby creating another data point. Steps 206-214 are repeated until a sufficient number of data points are created. In the illustrated embodiment, steps 206-214 are repeated for incrementally increasing coupling coefficients Kc. If a sufficient number of data points are created, e.g., when the expected best-case value of the coupling coefficient Kc is reached (step 216), a relationship between the respective amplitudes of the secondary signal and modulating signal is derived from the data points, which relationship represents the amplitudes of the secondary signal and modulating signal that maintains the uniform envelope signal Menv on the primary coil Lp (step 218). Such a relationship may, e.g., have a shape resembling the function illustrated in FIG. 11. Lastly, the sensor device 104 is manufactured with the secondary coil Ls, an amplitude detector configured for measuring the amplitude of a secondary carrier signal induced on the secondary coil, and processing circuitry configured for outputting a modulating signal in response to an input of the measured amplitude of the secondary carrier signal in accordance with the derived relationship, such that an envelope of the secondary carrier signal is load modulated (step 220). The processing circuitry may be analog in nature, such as the processing circuitry 144 illustrated in FIG. 10, in which case, the processing circuitry 144 may be tuned or calibrated in accordance with the data values generated in step 214, or the processing circuitry may be digital in nature, in which case, the data points generated in step 214 can be used to create a look-up table for storage in memory that can be subsequently accessed by the digital processing circuitry.

Figure 11:
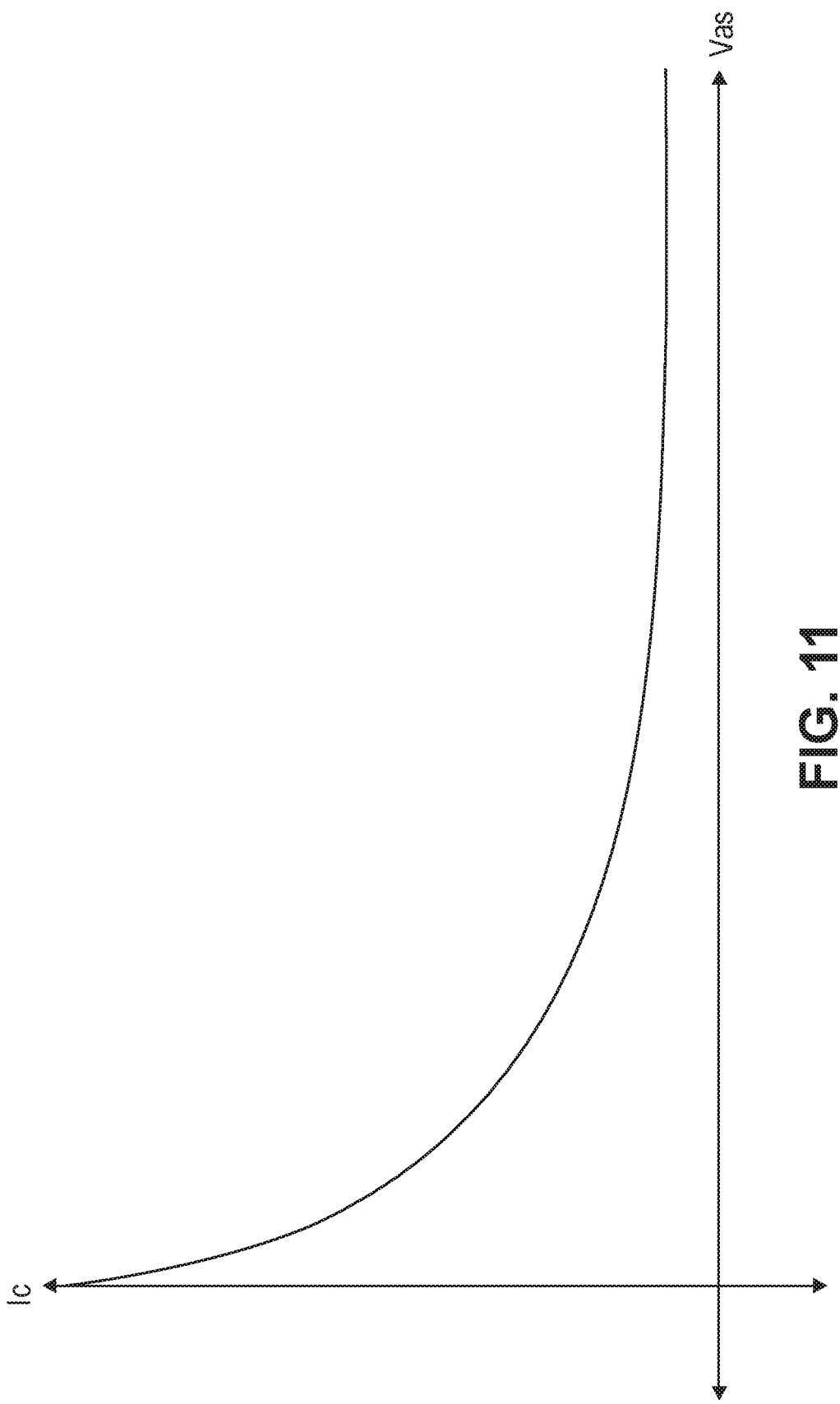
FIG. 11 is an exemplary function between the voltage amplitude of a secondary carrier signal and the amplitude of a modulating current generated by the telemetry/power circuitry of FIG. 10.

Although the relationship between the respective amplitudes of the secondary signal and the modulating signal is described as being derived from the data points generated in steps 202-218 for purposes of ensuring that the relationship is as accurate as possible for a particular geometry of the coils primary coil Lp and secondary coil Ls, it should be appreciated that in a simplified method, the relationship between the respective amplitudes of the secondary signal and the modulating signal can roughly be approximated from the function illustrated in FIG. 11.

Thus, it can be appreciated that the envelope signal (such as the envelope voltage Venv) induced on the primary coil 106 of the TC 102 when receiving uplink data from different sensor devices 104 with different coupling coefficients Kc will be automatically adjusted to a uniform value (e.g., uniform envelope voltage Menv).

Figure 13:
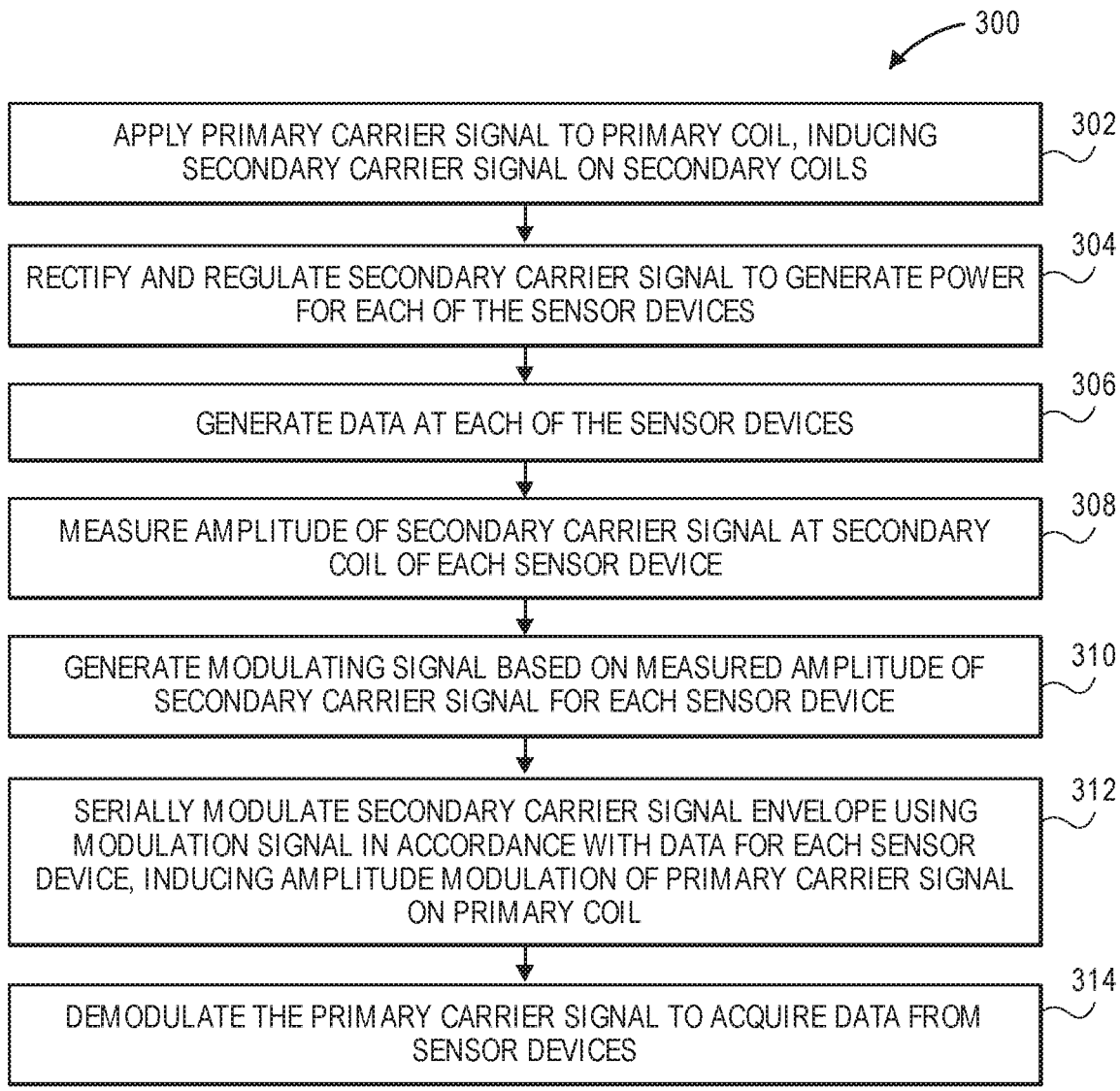
FIG. 13 is a flow diagram illustrating one method of communicating uplink data from the sensor devices to the telemetry controller of FIGS. 5a and 5b in a manner that equalizes the amplitude modulation on the primary carrier signal of the primary coil.

Having described the structure and function of the prosthetic control system 100, one method 300 of operating the prosthetic control system 100 to power the implanted sensor devices 104 (and in this case, sensor devices 104) and communicate physiological data, and in this case EMG data) of the patient 50 from the implanted sensor devices 104 to the TC 102 of the prosthetic control system 100 will be described with respect to FIGS. 10 and 13.

First, a primary alternating current (AC) carrier signal having an envelope is applied to the primary coil 106 of the TC 102, thereby respectively inducing a secondary carrier signal having an envelope on each of the secondary coils 108 of the respective implanted sensor devices 104 (step 302). The rectifier 132 rectifies the respective secondary carrier signal, and the regulator 134 regulates and supplies the power to the circuitry of each of the sensor devices 104 (step 304). Next, each of the sensor devices 104 generates data, e.g., by acquiring EMG data from adjacent muscles of the patient 50 via the respective electrodes 120 (step 306). Next, the amplitude of the secondary carrier signal (e.g., the peak voltage) on the secondary coil 108 of each of the sensor devices 104 is measured by the respective amplitude detector 138 (step 308). Notably, the amplitude of the secondary carrier signal is preferably measured, when unmodulated, and not measured during modulation. As such, measurement of the amplitude of the secondary carrier signal can be selectively performed by closing the switch S1 in the amplitude detector 138. Once such amplitude is measured, the switched S1 can be opened to essentially disconnect the amplitude detector 138 from the processing circuitry 140.

Next, in response to the measured amplitude of the unmodulated secondary carrier signal, the processing circuitry 140 of each sensor device 104 generates a modulating signal (e.g., a change in the current through the secondary coil 108) (step 310). Then, the uplink modulator 142 of each sensor device 104 serially load modulates the envelope of the secondary carrier signal on the respective secondary coil 108 in accordance with the data by selectively applying the modulation signal to the secondary coil 108 (i.e., applying the modulation signal to the secondary coil 108 in response to a "1" or "0" depending on the coding scheme) and not applying the modulation signal to the secondary coil 108 in response to the other of "1" or "0"), thereby inducing an amplitude modulation of the primary carrier signal envelope on the primary coil 106 (step 312).

The amplitude of the modulation signal generated by the processing circuitry 140 of each sensor device 104 is such that the variation of the amplitude modulation of the primary carrier signal envelope between sensor devices 104 is decreased relative to a variation between the coupling coefficients Kc, thereby compensating for the different coupling coefficients Kc between the primary coil 106 and the respective secondary coils 108. The amplitude modulation of the primary carrier signal envelope between the sensor devices 104 may be substantially uniform (e.g., less than 50% variation, and preferably less than 20% variation). For example, each of the secondary carrier signal envelopes is load modulated, such that the modulation magnitudes of the load modulated secondary carrier signal envelopes on the secondary coils 108 varies in an inversely varying relationship with the measured unmodulated carrier signal amplitudes (and thus, the respective coupling coefficients Kc) on the secondary coils 108.

Lastly, the uplink demodulator 156 of the TC 102 demodulates the modulated primary carrier signal envelope on the primary coil 106 to sequentially acquire the data from the sensor devices 104 (step 314). In the illustrated embodiment, the uplink demodulator demodulates the modulated primary carrier signal by detecting the modulating primary carrier signal envelope, and comparing it to the threshold level centered between a minimum and a maximum of the modulated primary carrier signal envelope.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A medical system, comprising:
   a telemetry controller comprising:
      a primary coil;
      a coil driver configured for applying a primary carrier signal having an envelope to the primary coil, the primary carrier signal envelope capable of being modulated; and
      a demodulator configured for amplitude demodulating the modulated primary carrier signal envelope to acquire data; and
   a plurality of implantable medical devices, each of which comprising:
      a secondary coil on which a secondary carrier signal having an envelope may be induced in response to the application of the primary carrier signal on the primary coil;
      an amplitude detector configured for measuring an amplitude of the secondary carrier signal;
      a modulator configured for amplitude modulating the secondary carrier signal envelope in accordance with data, thereby inducing an amplitude modulation of the primary carrier signal envelope on the primary coil,
   wherein the modulators of the implantable medical devices are configured for modulating their respective secondary carrier signal envelopes based on the measured amplitude of their respective secondary carrier signals, such that a variation of a peak-to-peak amplitude of the induced amplitude modulations of the primary carrier signal envelope between the implantable medical devices is decreased.

2. The medical system of claim 1, wherein the telemetry controller is an external telemetry controller.

3. The medical system of claim 1, wherein the measured amplitude of their respective secondary carrier signals comprises a peak amplitude of their respective secondary carrier signals.

4. The medical system of claim 1, wherein the demodulator is configured for amplitude demodulating the modulated primary carrier signal envelope by:
   detecting the induced amplitude modulations of the primary carrier signal envelope; and
   comparing the detected induced amplitude modulations of the primary carrier signal envelope to a threshold level.

5. The medical system of claim 4, wherein an amplitude of the threshold level is between a minimum and a maximum of the modulated primary carrier signal envelope.

6. The medical system of claim 5, wherein the amplitude of the threshold level is centered between the minimum and the maximum of the modulated primary carrier signal envelope.

7. The medical system of claim 1, wherein the induced amplitude modulations of the primary carrier signal envelope are substantially uniform for the implantable medical devices.

8. The medical system of claim 7, wherein a variation in the induced amplitude modulations of the primary carrier signal envelope between the implantable medical devices is less than 50%.

9. The medical system of claim 7, wherein a variation in the induced amplitude modulations of the primary carrier signal envelope between the implantable medical devices is less than 20%.

10. The implantable medical system of claim 1, wherein the modulators are configured for modulating the envelope of their respective secondary carrier signals, such that modulation magnitudes of the modulated envelope of their respective secondary carrier signals vary in an inversely varying relationship with coupling coefficients between their respective secondary coils and the primary coil.

11. The medical system of claim 1, wherein the amplitude detector of each of the implantable medical devices is configured for measuring the amplitude of their respective secondary carrier signals on their respective secondary coils by measuring a voltage across their respective secondary coils, and the modulator of each of the implantable medical devices is configured for amplitude modulating the envelope of their respective secondary carrier signals by modifying a load current associated with their respective secondary coils as a function of the measured voltage.

12. The medical system of claim 1, wherein each of the implantable medical devices further comprises a rectifier configured for rectifying and regulating their respective secondary carrier signals for powering circuitry within their respective implantable medical devices.

13. The implantable medical system of claim 1, wherein the modulators are configured for load modulating their respective secondary carrier signal envelopes.

14. The medical system of claim 1, wherein the data is physiological data of a patient, wherein each of the implantable medical devices further comprises at least one sensor configured for acquiring the physiological data from the patient.

15. The medical system of claim 1, wherein the data is operational status data of each of the implantable medical devices.

16. A method of communicating between a telemetry controller and a plurality of medical devices implanted within a patient, the telemetry controller having a primary coil and each of the medical devices has a secondary coil, wherein coupling coefficients between the primary coil and the secondary coils differ from each other, the method comprising:
applying a primary carrier signal having an envelope to the primary coil, thereby respectively inducing a secondary carrier signal having an envelope on each of the secondary coils;
generating data by each of the implanted medical devices;
measuring an amplitude of the secondary carrier signal on each of the secondary coils;
sequentially amplitude modulating each of the secondary carrier signal envelopes in accordance with the data generated by the respective implanted medical devices, thereby inducing amplitude modulations of the primary carrier signal envelope on the primary coil for the implanted medical devices, wherein the secondary carrier signal envelopes are modulated based on the measured amplitudes of the respective secondary carrier signals, such that a variation of a peak-to-peak amplitude of the induced amplitude modulations of the primary carrier signal envelope between the implanted medical devices is decreased; and
amplitude demodulating the induced amplitude modulations of the primary carrier signal envelope to acquire the data from the implanted medical devices.

17. The method of claim 16, wherein the telemetry controller is external to the patient.

18. The method of claim 16, wherein the measured amplitudes of the secondary carrier signals comprise peak amplitudes of the secondary carrier signals.

19. The method of claim 16, wherein amplitude demodulating the induced amplitude modulations of the primary carrier signal envelope comprises:
detecting the induced amplitude modulations of the primary carrier signal envelope; and
comparing the detected induced amplitude modulations of the primary carrier signal envelope to a threshold level.

20. The method of claim 19, wherein an amplitude of the threshold level is centered between a minimum and a maximum of the induced amplitude modulations of the primary carrier signal envelope.

21. The method of claim 16, wherein the induced amplitude modulations of the primary carrier signal envelope are substantially uniform for the implanted medical devices.

22. The method of claim 21, wherein a variation in the induced amplitude modulations of the primary carrier signal envelope between the implanted medical devices is less than 50%.

23. The method of claim 21, wherein a variation in the induced amplitude modulations of the primary carrier signal envelope between the implanted medical devices is less than 20%.

24. The method of claim 16, wherein each of the secondary carrier signal envelopes is modulated, such that modulation magnitudes of the modulated envelopes of the secondary carrier signals vary in an inversely varying relationship with the coupling coefficients between the respective secondary coils and the primary coil.

25. The method of claim 16, wherein measuring the amplitude of the secondary carrier signal on each of the secondary coils comprises measuring a voltage across the respective secondary coils, and wherein amplitude modulating the envelope of each of the secondary carrier signals comprises modifying a load current associated with the respective secondary coils as a function of the measured voltage.

26. The method of claim 16, further comprising generating power for each of the implanted medical devices from the respective secondary carrier signals.

27. The method of claim 16, wherein amplitude modulating each of the secondary carrier signal envelopes comprises load modulating each of the secondary carrier signal envelopes.

28. The method of claim 16, wherein the generated data is physiological data acquired from the patient by each of the implanted medical devices.

29. The method of claim 16, wherein the generated data is operational status data of each of the implanted medical devices.

* * * * *